US011857188B2

(12) United States Patent
Hites

(10) Patent No.: US 11,857,188 B2
(45) Date of Patent: Jan. 2, 2024

(54) ARTICULATION ASSEMBLIES FOR SURGICAL INSTRUMENTS

(71) Applicant: INTUITIVE SURGICAL OPERATIONS, INC., Sunnyvale, CA (US)

(72) Inventor: Tibor Hites, San Lorenzo, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 249 days.

(21) Appl. No.: 17/414,714

(22) PCT Filed: Nov. 20, 2019

(86) PCT No.: PCT/US2019/062344
§ 371 (c)(1),
(2) Date: Jun. 16, 2021

(87) PCT Pub. No.: WO2020/131290
PCT Pub. Date: Jun. 25, 2020

(65) Prior Publication Data
US 2022/0061840 A1 Mar. 3, 2022

Related U.S. Application Data

(60) Provisional application No. 62/783,481, filed on Dec. 21, 2018.

(51) Int. Cl.
*A61B 17/072* (2006.01)
*A61B 34/30* (2016.01)
*A61B 17/00* (2006.01)

(52) U.S. Cl.
CPC ........ *A61B 17/07207* (2013.01); *A61B 34/30* (2016.02); *A61B 2017/00367* (2013.01);
(Continued)

(58) Field of Classification Search
CPC .... A61B 2017/2927; A61B 2017/2932; A61B 2017/2939; A61B 2017/2943; B25J 17/02
(Continued)

(56) References Cited

U.S. PATENT DOCUMENTS 4,305,539 A 12/1981 Korolkov et al.
4,319,576 A 3/1982 Rothfuss
(Continued)

FOREIGN PATENT DOCUMENTS

EP 0277532 B1 8/1990
EP 0277529 B1 4/1993
(Continued)

OTHER PUBLICATIONS

International Search Report and Written Opinion for Application No. PCT/US2020/054568, dated Jan. 29, 221, 13 pages.
(Continued)

*Primary Examiner* — Valentin Neacsu
(74) *Attorney, Agent, or Firm* — Farber, LLC

(57) ABSTRACT

The present disclosure provides a surgical instrument, such as a tissue sealing instrument, with an elongate shaft and an end effector movably coupled to the shaft with a joint or wrist assembly. The wrist assembly includes a first outer link, a second outer link, and an inner link. The first outer link is connected to the elongated shaft and movably coupled to the second outer link by the inner link. The inner link includes a pair of posts, and the first and second outer links each include a recess configured to receive a respective one of the pair of posts. The posts and recesses defining a rocking hinge, which permits the wrist assembly to accommodate a reduction in the size of the rolling radius to reduce the likelihood of grabbing and pinching tissue during articulation of the end effector without sacrificing the internal bend radius of the hinge joint.

18 Claims, 18 Drawing Sheets

(52) U.S. Cl.
CPC ............... *A61B 2017/00477* (2013.01); *A61B 2017/07278* (2013.01); *A61B 2034/306* (2016.02)

(58) Field of Classification Search
USPC ................ 227/176.1, 175.1; 901/27, 28, 29; 74/490.06, 490.05, 490.01
See application file for complete search history.

(56) References Cited

U.S. PATENT DOCUMENTS

| | | |
|---|---|---|
| 4,407,286 A | 10/1983 | Noiles et al. |
| 4,429,695 A | 2/1984 | Green |
| 4,509,518 A | 4/1985 | McGarry et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,133,735 A | 7/1992 | Slater et al. |
| 5,133,736 A | 7/1992 | Bales, Jr. et al. |
| 5,147,357 A | 9/1992 | Rose et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,395 A | 8/1994 | Jarrett et al. |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,564,615 A | 10/1996 | Bishop et al. |
| 5,571,116 A | 11/1996 | Bolanos et al. |
| 5,571,285 A | 11/1996 | Chow et al. |
| 5,573,534 A | 11/1996 | Stone |
| 5,615,820 A | 4/1997 | Viola |
| 5,624,452 A | 4/1997 | Yates |
| 5,628,446 A | 5/1997 | Geiste et al. |
| 5,651,491 A | 7/1997 | Heaton et al. |
| 5,652,849 A | 7/1997 | Conway et al. |
| 5,667,626 A | 9/1997 | Cayford et al. |
| 5,673,842 A | 10/1997 | Bittner et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,700,270 A | 12/1997 | Peyser et al. |
| 5,700,276 A | 12/1997 | Benecke |
| 5,709,680 A | 1/1998 | Yates et al. |
| 5,752,644 A | 5/1998 | Bolanos et al. |
| 5,752,973 A | 5/1998 | Kieturakis et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,050,996 A | 4/2000 | Schmaltz et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 | 12/2002 | Fenton, Jr. |
| 6,503,259 B2 | 1/2003 | Huxel et al. |
| 6,585,735 B1 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,258,262 B2 | 8/2007 | Mastri et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,654,431 B2 | 2/2010 | Hueil et al. |
| 7,658,312 B2 | 2/2010 | Vidal et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,794,475 B2 | 9/2010 | Hess et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |

(56) References Cited

U.S. PATENT DOCUMENTS

| | | |
|---|---|---|
| 8,348,127 B2 | 1/2013 | Marczyk |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,864,010 B2 | 10/2014 | Williams |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 11,234,700 B2 * | 2/2022 | Ragosta .................. A61B 34/71 |
| 11,439,390 B2 | 9/2022 | Patel et al. |
| 11,504,124 B2 | 11/2022 | Patel et al. |
| 11,517,312 B2 | 12/2022 | Wixey |
| 11,642,129 B2 | 5/2023 | Burbank |
| 2002/0165562 A1 | 11/2002 | Grant et al. |
| 2003/0135204 A1 | 7/2003 | Lee et al. |
| 2003/0181910 A1 | 9/2003 | Dycus et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0178813 A1 | 8/2005 | Swayze et al. |
| 2005/0187576 A1 | 8/2005 | Whitman et al. |
| 2005/0273084 A1 * | 12/2005 | Hinman .................. A61B 90/11 606/1 |
| 2005/0273085 A1 * | 12/2005 | Hinman ............ A61M 25/0138 606/1 |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 * | 5/2006 | Hinman .................. A61B 17/28 474/206 |
| 2006/0111210 A1 * | 5/2006 | Hinman .................. A61B 17/32 474/206 |
| 2006/0161190 A1 | 7/2006 | Gadberry et al. |
| 2006/0190031 A1 | 8/2006 | Wales et al. |
| 2006/0217706 A1 | 9/2006 | Lau et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0250113 A1 * | 10/2007 | Hegeman ............ A61B 1/0055 606/207 |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2008/0086114 A1 | 4/2008 | Schmitz et al. |
| 2009/0277947 A1 | 11/2009 | Viola |
| 2010/0006620 A1 | 1/2010 | Sorrentino et al. |
| 2010/0076474 A1 | 3/2010 | Yates et al. |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0331857 A1 * | 12/2010 | Doyle .................. A61B 34/30 901/29 |
| 2011/0022078 A1 * | 1/2011 | Hinman ............ A61B 17/2909 403/123 |
| 2011/0118707 A1 * | 5/2011 | Burbank ................ A61B 34/37 606/1 |
| 2011/0152879 A1 * | 6/2011 | Williams ................ A61B 34/71 606/130 |
| 2011/0174863 A1 | 7/2011 | Shelton, IV et al. |
| 2011/0251612 A1 | 10/2011 | Faller et al. |
| 2011/0251613 A1 | 10/2011 | Guerra et al. |
| 2011/0290851 A1 | 12/2011 | Shelton, IV |
| 2011/0290854 A1 | 12/2011 | Timm et al. |
| 2011/0295270 A1 * | 12/2011 | Giordano ......... A61B 17/07207 606/130 |
| 2011/0301603 A1 | 12/2011 | Kerr et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0223121 A1 | 9/2012 | Viola et al. |
| 2012/0228358 A1 | 9/2012 | Zemlok et al. |
| 2012/0248167 A1 | 10/2012 | Flanagan et al. |
| 2012/0255986 A1 | 10/2012 | Petty et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1 | 4/2013 | Kostrzewski et al. |
| 2013/0126586 A1 * | 5/2013 | Zhang .................. A61B 17/068 227/176.1 |
| 2013/0148577 A1 | 6/2013 | Terry et al. |
| 2013/0248577 A1 * | 9/2013 | Leimbach ............ A61B 17/105 227/176.1 |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 * | 1/2014 | Shelton, IV ...... A61B 17/07207 227/176.1 |
| 2014/0005653 A1 * | 1/2014 | Shelton, IV ........... A61B 18/14 606/205 |
| 2014/0021239 A1 | 1/2014 | Kostrzewski |
| 2014/0025071 A1 | 1/2014 | Sims et al. |
| 2014/0100600 A1 | 4/2014 | Kendrick |
| 2014/0175152 A1 | 6/2014 | Hess et al. |
| 2014/0180286 A1 | 6/2014 | Marczyk et al. |
| 2014/0200596 A1 | 7/2014 | Weir et al. |
| 2014/0214049 A1 * | 7/2014 | Jeong ............ A61B 17/00234 606/130 |
| 2014/0257331 A1 * | 9/2014 | Kim ...................... A61B 34/30 606/130 |
| 2014/0263546 A1 | 9/2014 | Aranyi |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0284372 A1 | 9/2014 | Kostrzewski |
| 2014/0343550 A1 | 11/2014 | Faller et al. |
| 2014/0343569 A1 | 11/2014 | Turner |
| 2014/0364851 A1 | 12/2014 | Batross et al. |
| 2015/0173789 A1 | 6/2015 | Baxter, III et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |

(56) References Cited

U.S. PATENT DOCUMENTS

| | | |
|---|---|---|
| 2015/0272576 A1 | 10/2015 | Cappola |
| 2015/0297227 A1 | 10/2015 | Huitema et al. |
| 2015/0297235 A1 | 10/2015 | Harris et al. |
| 2016/0038227 A1 | 2/2016 | Garrison |
| 2016/0058450 A1 | 3/2016 | Shelton, IV et al. |
| 2016/0066916 A1 | 3/2016 | Overmyer et al. |
| 2016/0120544 A1 | 5/2016 | Shelton, IV et al. |
| 2016/0157863 A1 | 6/2016 | Williams et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |
| 2018/0021042 A1 | 1/2018 | Nicholas et al. |
| 2018/0161052 A1* | 6/2018 | Weir .......... A61B 34/00 |
| 2018/0168581 A1 | 6/2018 | Hunter et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0296213 A1 | 10/2018 | Strobl |
| 2018/0310948 A1 | 11/2018 | Stamm et al. |
| 2018/0317915 A1 | 11/2018 | McDonald, II |
| 2019/0000454 A1 | 1/2019 | Swayze et al. |
| 2019/0015124 A1 | 1/2019 | Williams et al. |
| 2019/0059894 A1 | 2/2019 | Kumada et al. |
| 2019/0083086 A1 | 3/2019 | Klaffenböck et al. |
| 2019/0099181 A1 | 4/2019 | Shelton, IV et al. |
| 2019/0125347 A1 | 5/2019 | Stokes et al. |
| 2019/0142531 A1 | 5/2019 | Wentworth et al. |
| 2019/0201146 A1 | 7/2019 | Shelton, IV et al. |
| 2019/0231350 A1 | 8/2019 | Scott et al. |
| 2019/0239877 A1* | 8/2019 | Ragosta ............. A61B 34/71 |
| 2019/0239881 A1 | 8/2019 | Laurent et al. |
| 2019/0290374 A1 | 9/2019 | Ramadorai |
| 2019/0298356 A1 | 10/2019 | Shelton, IV et al. |
| 2019/0314107 A1* | 10/2019 | Worrell ............. A61B 90/90 |
| 2019/0365458 A1 | 12/2019 | Whitlock et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0267596 A1 | 9/2021 | Fanelli et al. |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1* | 3/2022 | Hites ............. A61B 34/37 |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1* | 4/2022 | Ragosta ........... A61B 17/07207 |
| 2022/0160358 A1 | 5/2022 | Wixey |
| 2022/0183686 A1 | 6/2022 | Wixey et al. |
| 2022/0192665 A1 | 6/2022 | Wellman |
| 2022/0346790 A1 | 11/2022 | Wellman |
| 2022/0378537 A1* | 12/2022 | Hites .......... B25J 17/00 |
| 2022/0395270 A1 | 12/2022 | Patel et al. |
| 2023/0020577 A1 | 1/2023 | Kerver et al. |
| 2023/0047784 A1 | 2/2023 | Patel et al. |
| 2023/0052074 A1 | 2/2023 | Wixey |

FOREIGN PATENT DOCUMENTS

| | | |
|---|---|---|
| EP | 0641546 A1 | 3/1995 |
| EP | 1090592 A1 | 4/2001 |
| EP | 1728473 A1 | 12/2006 |
| EP | 1479346 B1 | 1/2007 |
| EP | 1621141 B1 | 7/2007 |
| EP | 1316290 B1 | 2/2012 |
| EP | 1754445 B1 | 10/2013 |
| EP | 3135225 A2 | 3/2017 |
| EP | 3158947 A1 | 4/2017 |
| EP | 3173029 A1 | 5/2017 |
| FR | 2828952 B1 | 12/2005 |
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2012142872 A1 | 10/2012 |
| WO | WO-2014106275 A1 | 7/2014 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |

OTHER PUBLICATIONS

International Preliminary Report on Patentability for Application No. PCT/US2019/017646, dated Aug. 27, 2020, 10 pages.

International Preliminary Report on Patentability for Application No. PCT/US2019/019501, dated Sep. 3, 2020, 7 pages.

International Search Report and Written Opinion for Application No. PCT/US2020/025655, dated Jul. 22, 2020, 8 pages.

International Search Report and Written Opinion for Application No. PCT/US19/17646, dated Apr. 16, 2019, 11 pages.

International Search Report and Written Opinion for Application No. PCT/US2019/019501, dated May 9, 2019, 8 pages.

International Search Report and Written Opinion for Application No. PCT/US2019/056979, dated Dec. 18, 2019, 8 pages.

International Search Report and Written Opinion for Application No. PCT/US2019/062344, dated Mar. 23, 2020, 17 pages.

International Search Report and Written Opinion for Application No. PCT/US2019/062768, dated Mar. 9, 2020, 15 pages.

International Search Report and Written Opinion for Application No. PCT/US2019/064861, dated Mar. 30, 2020, 18 pages.

(56) References Cited

OTHER PUBLICATIONS

International Search Report and Written Opinion for Application No. PCT/US2019/066513, dated Apr. 21, 2020, 8 pages.
International Search Report and Written Opinion for Application No. PCT/US2019/066530, dated Apr. 21, 2020, 8 pages.
International Search Report and Written Opinion for Application No. PCT/US2020/020672, dated Jun. 29, 2020, 10 pages.
International Search Report and Written Opinion for Application No. PCT/US2020/033481, dated Sep. 3, 2020, 22 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
European Search Report (Corrected version) for Application No. EP19750317.0, dated Mar. 28, 2022, 26 pages.
Partial European Search Report for Application No. EP19757451.0, dated Feb. 2, 2022, 12 pages.
International Search Report and Written Opinion for Application No. PCT/US2021/012284, dated May 6, 2021, 23 pages.
Supplementary European Search Report for Application No. EP19873128.3, dated Jun. 22, 2022, 7 pages.

\* cited by examiner

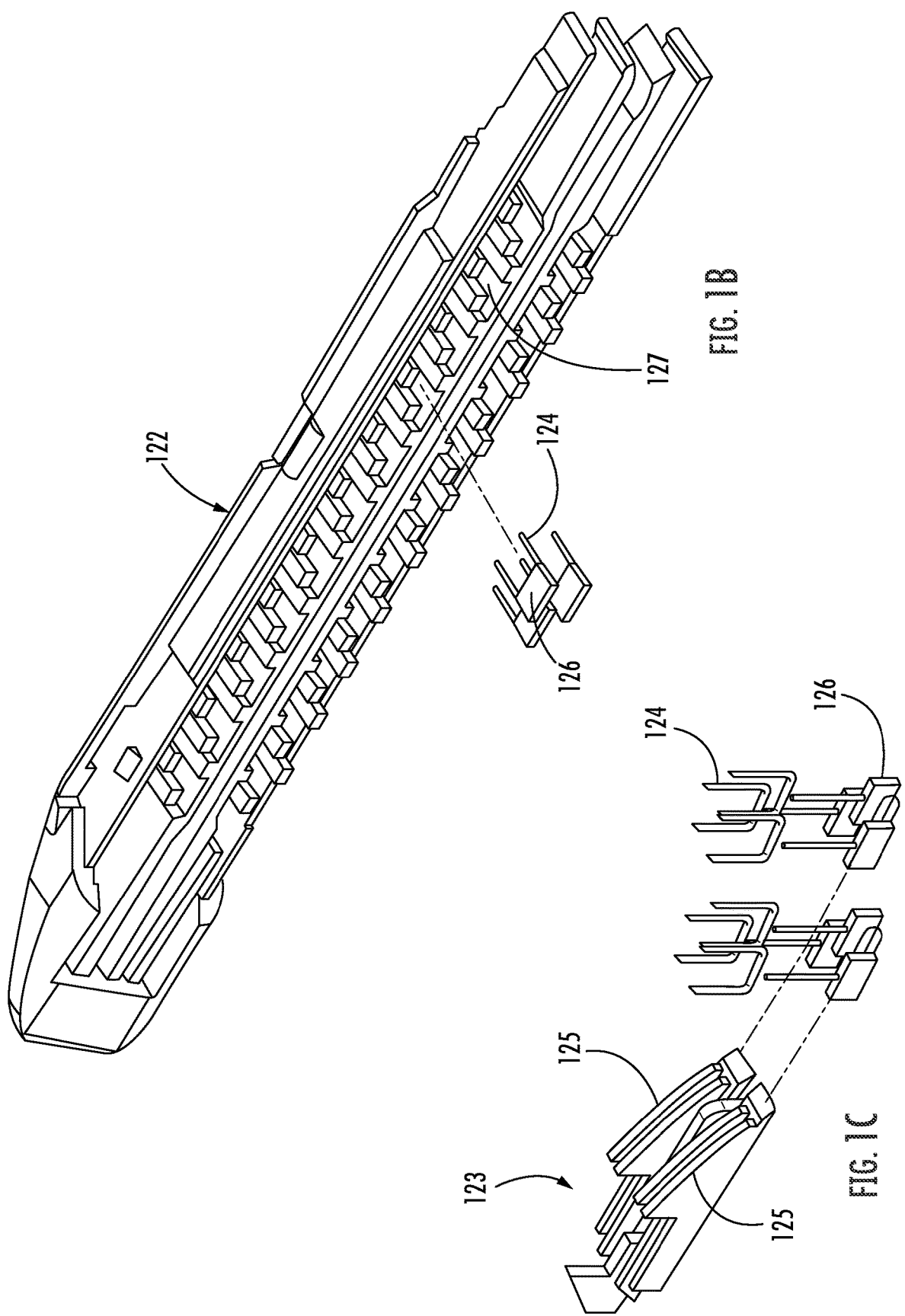

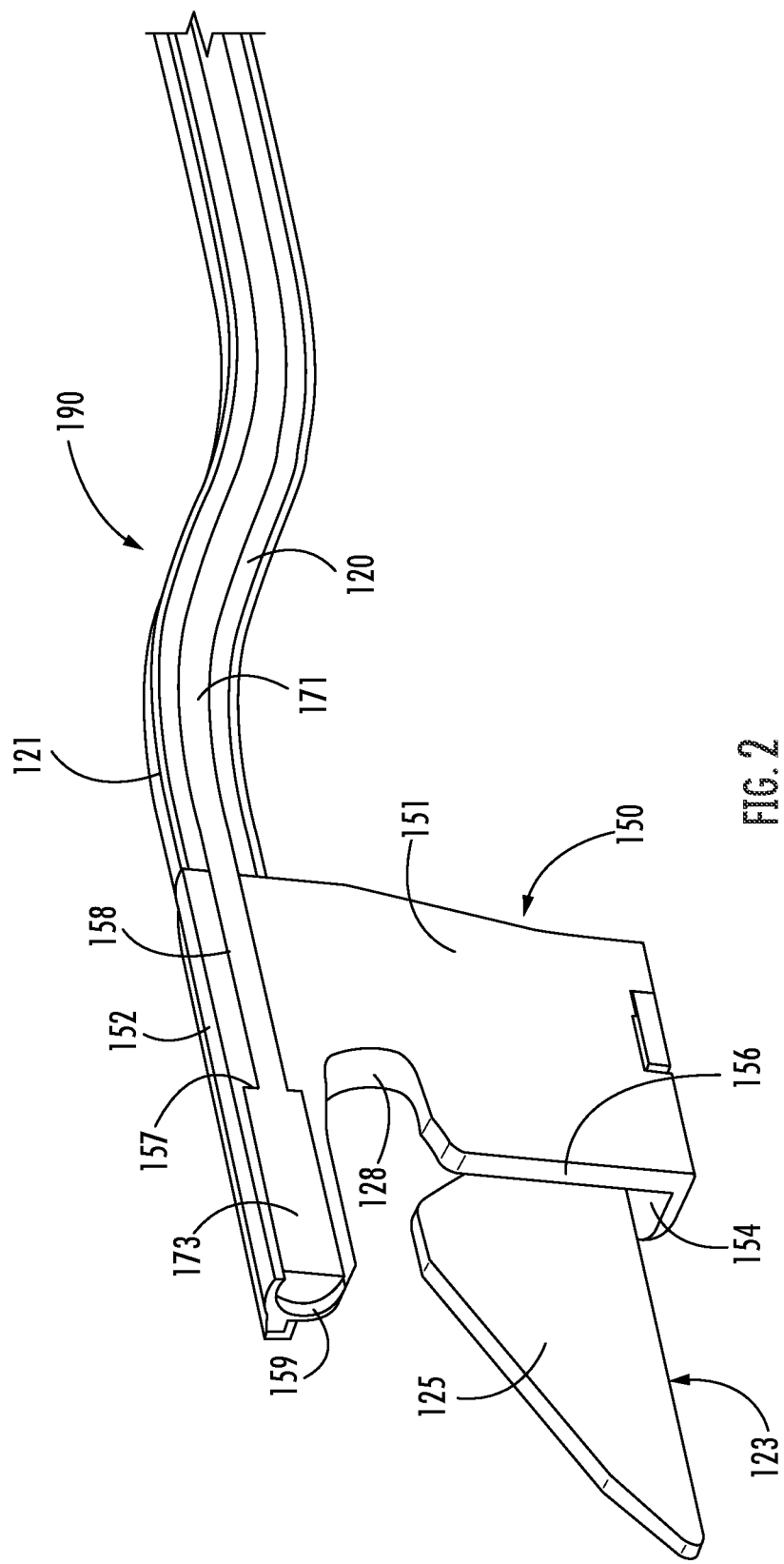

ARTICULATION ASSEMBLIES FOR SURGICAL INSTRUMENTS

CROSS REFERENCE TO RELATED APPLICATIONS

This application is the National Stage of International Application No. PCT/US2019/062344 filed Nov. 20, 2019, which claims benefit of U.S. Provisional Application No. 62/783,481, filed Dec. 21, 2018, the entire disclosure of which is incorporated herein by reference for all purposes.

BACKGROUND

The field of the present disclosure relates to medical instruments, and more particularly to tissue sealing instruments for use in surgeries. Even more particularly, the present disclosure relates to a surgical stapling instrument having a novel wrist assembly for articulating an end effector at the distal end of the instrument.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms. A surgical instrument is mounted on each of the robotic arms. Operative communication between master controllers and associated robotic arm and instrument assemblies is typically achieved through a control system. The control system typically includes at least one processor that relays input commands from the master controllers to the associated robotic arm and instrument assemblies and back in the case of, for example, force feedback or the like. One example of a robotic surgical system is the DA VINCI™ system commercialized by Intuitive Surgical, Inc. of Sunnyvale, Calif.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912, 6,758,843, 6,246,200, and 5,800,423, the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. Nos. 6,702,805, 6,676,669, 5,855,583, 5,808,665, 5,445,166, and 5,184,601, the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide two or three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical instruments are often deployed into restrictive body cavities (e.g., through a cannula to inside the pelvis). Accordingly, it is desirable for the surgical instrument to be both compact and maneuverable for best access to and visibility of the surgical site. Known surgical instruments, however, may fail to be both compact and maneuverable. For example, known surgical instruments may lack maneuverability with respect to multiple degrees of freedom (e.g., Roll, Pitch, and Yaw) and associated desired ranges of motion.

Articulating mechanisms allow a clinician to remotely steer and guide and/or manipulate the end effector of such surgical instruments. Typically, a drive mechanism extends through the articulation mechanism to advance, retract or otherwise manipulate components of the end effector. The articulation mechanism typically includes hinges that allow the clinician to direct the end effector in multiple directions to reach the surgical site. Such articulation mechanisms are particularly useful when attempting to navigate a workspace that is not easy to manually navigate by hand.

One of the drawbacks with conventional hinges in surgical instruments is that tissue can become trapped and pinched between the pivotable links on the hinge as the end effector is articulated relative to the instrument shaft. In order to reduce the likelihood of such tissue pinching, the size of the rolling radius (i.e., the distance from the center to the outer diameter) of each of the hinge links can be reduced. In conventional fixed hinge designs, however, when the size of the rolling radius of the various links of the articulation mechanism are reduced, the link length is shortened, thereby reducing the internal bend radius that the articulation mechanism can accommodate. This reduced bend radius decreases the efficiency of the drive mechanism, increases shear wear on the components of the drive mechanism, and will generally increase the input forces required for steering (if, for example, the wrist joint has any intrinsic bending stiffness).

To reduce or eliminate the risk of tissue pinching, a wrist cover can be placed around the articulation assembly of the surgical instrument. The wrist cover, however, effectively reduces the diameter of the internal articulation assembly (or increases the diameter of the surgical instrument at the wrist joint). In addition, a wrist cover reduces mechanical strength, wrist stability (twitch) and increases the input forces required for steering.

Accordingly, while the new telesurgical systems and devices have proven highly effective and advantageous, still further improvements would be desirable. In general, it would be desirable to provide improved surgical instruments that are more compact and maneuverable to enhance the efficiency and ease of use of minimally invasive systems. More specifically, it would be beneficial to provide improved hinge joints for articulating end effectors on surgical instruments that can reduce the likelihood of tissue pinching, while maintaining or improving the internal bend radius of the hinge joint.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to a wrist assembly for articulating an end effector relative to a shaft of a surgical instrument. In one aspect, the links of the wrist assembly form a rocking hinge which permits the articulating mechanism to accommodate a reduction in the size of the rolling radius of the wrist assembly without requiring an accompanying reduction in link length, thereby preserving the internal bend radius of the wrist assembly. This allows for the design of wrist assemblies that reduce the likelihood of grabbing and pinching tissue during articulation of the end effector without sacrificing the internal bend radius of the hinge joint. A larger internal bend radius increases the efficiency of the drive mechanism, decreases shear wear on the components of the drive mechanism, and will generally reduce the steering input forces (in the event that the wrist joint has any intrinsic bending stiffness).

In embodiments, a wrist assembly in accordance with this disclosure includes a first outer link, a second outer link, and a first inner link. The first outer link is connected to an elongated shaft and movably coupled to the second outer link by the first inner link such that the end effector can be articulated about an axis substantially perpendicular to the longitudinal axis of the instrument shaft. The first inner link includes a pair of posts, and the first and second outer links each include a recess configured to receive a respective one of the pair of posts. The posts and recesses define a rocking hinge.

The center of the posts on the inner link are preferably movable within the recesses relative to the outer links (i.e., in addition to rotating, the center of the posts translate relative to the first and second outer links). This allows the centerline between the inner link posts to move away from the centerline of the rolling radius centers of the outer links during articulation of the joint, providing a rocking hinge. The rocking hinge of the present invention allows for reduction in the rolling radius of each outer link, while preserving the internal bend radius of the overall wrist assembly.

In embodiments, the pair of posts on the first inner link are substantially rectangular. In embodiments, the first inner link includes two pairs of posts. In embodiments, the first and second outer links include gear teeth that intermesh.

In embodiments, the wrist assembly further includes a third outer link and a second inner link, the second outer link being movably coupled to the third outer link by the second inner link. The three outer links provide two degrees of freedom for the wrist assembly. In embodiments, the third outer link is connected to the end effector. In embodiments, the second inner link includes a post and the third outer link includes a recess configured to receive the post of the second inner link, the post of the second inner link and the recess of the third outer link defining a rocking hinge. In embodiments, the second inner link includes two pairs of posts.

In certain embodiments, the rolling radius of each link is reduced while maintaining the overall pivot length of the middle outer link. This results in an increased link or disk length, which can significantly improve the mechanical strength of the middle outer link and allow for a more compact design. In other embodiments, the rolling radius of the link can be reduced without increasing the disk length. This results in a reduced middle outer link length, thereby yielding a more compact wrist assembly. In another aspect, a surgical instrument in accordance with this disclosure includes an elongated shaft and an end effector. The surgical instrument further includes a wrist assembly movably connecting the end effector to the elongated shaft. The wrist assembly includes a first outer link, a second outer link, and a first inner link. The first outer link is connected to an elongated shaft and movably coupled to the second outer link by the first inner link. The first inner link includes a pair of posts, and the first and second outer links each include a recess configured to receive a respective one of the pair of posts. The posts and recesses define a rocking hinge.

In embodiments, the pair of posts on the first inner link are substantially rectangular. In embodiments, the first inner link includes two pairs of posts. In embodiments, the first and second outer links include gear teeth that intermesh. The gear teeth provide enhanced timing to assist with accurately positioning the outer links (i.e., returning the outer links a neutral position (e.g., zero angle roll alignment). In addition, the gear teeth enhance the smoothness of the motion between the outer links when the outer links are reoriented relative to one another In embodiments, the wrist assembly further includes a third outer link and a second inner link, the second outer link being movably coupled to the third outer link by the second inner link. In embodiments, the third outer link is connected to the end effector. The second and third outer links preferably allow for articulation of the end effector about a second axis substantially perpendicular to the instrument shaft (i.e., providing the end effector with articulation about both a pitch and a yaw axis relative to the shaft).

In embodiments, the second inner link includes a post and the third outer link includes a recess configured to receive the post of the second inner link, the post of the second inner link and the recess of the third outer link defining a rocking hinge. In embodiments, the second inner link includes two pairs of posts.

In embodiments, the surgical instrument further includes a drive mechanism extending through the wrist assembly. In embodiments, the drive mechanism is configured for operation by a robotic surgical system. In embodiments, the drive mechanism is configured for operation by an electro-mechanical powered instrument. In embodiments, the drive mechanism is configured for operation by a manually powered instrument.

In embodiments, the end effector includes a pair of jaws configured to grasp tissue. In embodiments, the end effector includes a pair of jaws configured to staple and cut tissue.

In another aspect of the invention, a surgical instrument comprises an elongated shaft extending along a first axis, an end effector and a joint assembly movably coupling the end effector to the elongated shaft. The joint assembly includes a first outer link, a second outer link and an inner link movably coupling the first outer link to the second outer link. The inner link comprises first and second posts pivotally coupling the inner link to the first and second outer links, respectively. The center of each of the first and second posts is movable relative to the first and second outer links during articulation of the first outer link relative to the second outer link.

In a preferred embodiment, the first and second outer links have first and second recesses for receiving the first and second posts, respectively, and the center of the first and second posts move within the first and second recesses during articulation of the first outer link relative to the second outer link. The inner cross-sectional area of the recesses is larger than a cross-sectional area of the posts, allowing movement of the posts within the first and second recesses.

In an exemplary embodiment, the first and second outer links each define a rolling radius with a center and a centerline therebetween. The centerline extending between the center of each of the posts is not coincident with the centerline between the rolling radii of each of the first and second outer links during articulation of the first outer link relative to the second outer link. Specifically, the centerline between the posts moves away from the rolling radius centerline in the direction of articulation.

In certain embodiments, the end effector comprises a first jaw and a second jaw configured to move relative to each other from an open position to a closed position. The surgical instrument may comprise a linear stapling instrument having a staple cartridge coupled to one of the first and second jaws and housing a plurality of staples. Preferably, a drive member extends through the joint assembly and is configured to translate distally through the end effector. The drive member engages the staples upon distal translation of the drive member through the staple cartridge and move the staples from an interior of the staple cartridge to an exterior of the staple cartridge to drive the staples into tissue.

The instrument may include an actuation mechanism in contact with the drive member and configured to translate the drive member distally through the end effector and an actuator operatively coupled to the actuation mechanism. The actuator may include a control device of a robotic surgical system.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The above and other aspects, features, and advantages of the present surgical instruments will become more apparent in light of the following detailed description when taken in conjunction with the accompanying drawings in which:

FIG. 1B is a bottom perspective view with parts separated of a representative staple cartridge for an illustrative surgical instrument;

FIG. 1C shows an enlarged view of the cooperative relationship between a portion of a drive member and a plurality of staple pushers and staples which form part of the staple cartridge of FIG. 1B;

FIG. 2 is a partial cross-sectional view of the actuation mechanism for a drive member in accordance with the surgical instrument of FIG. 1;

DETAILED DESCRIPTION

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail.

While the following disclosure is presented with respect to a linear surgical stapler where staples are sequentially fired, it should be understood that the features of the presently described surgical instruments may be readily adapted for use in any type of surgical grasping, clamping, cutting, or sealing instruments, whether or not the surgical clamping and cutting instrument applies a fastener. For example, the presently described drive member and actuation mechanism may be employed in an electrosurgical instrument wherein the jaws include electrodes for applying energy to tissue to treat (e.g., cauterize, ablate, fuse, or cut) the tissue. The surgical clamping and cutting instrument may be a minimally invasive (e.g., laparoscopic) instrument or an instrument used for open surgery. Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

Figure 1:
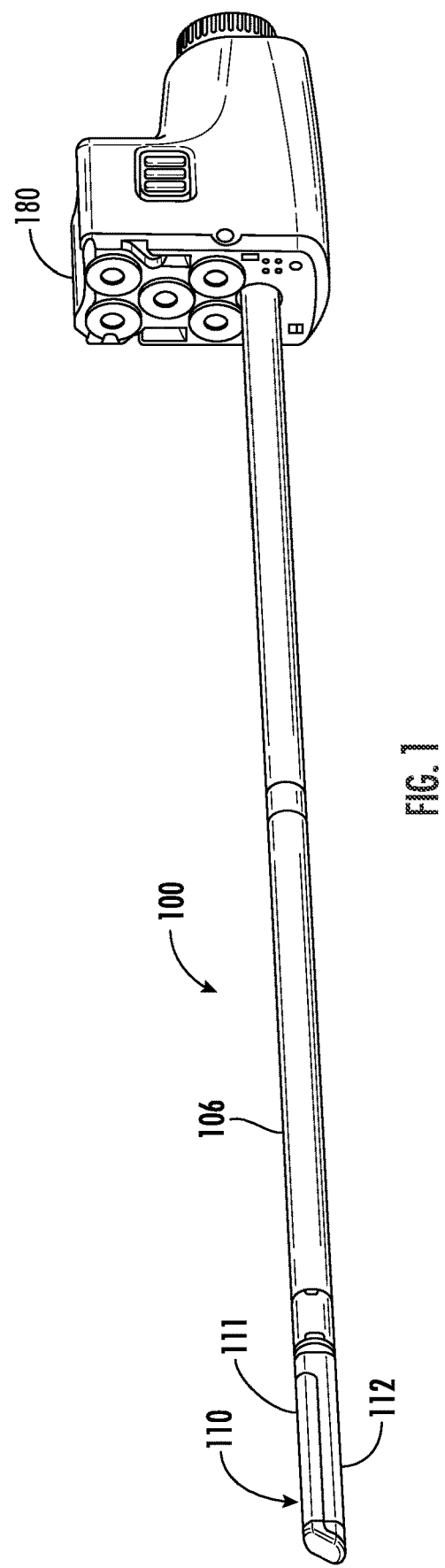
FIG. 1 is a perspective view of an illustrative surgical instrument in accordance with the present disclosure.

FIG. 1 is a perspective view of a representative surgical instrument 100 in accordance with embodiments of the present disclosure having a proximal mechanism that may include input couplers 180 on a handle assembly, and an end effector 110 mounted on an elongated shaft 106. Input couplers 180 typically provide a mechanical coupling between the drive tendons or cables of the instrument and motorized axes of the mechanical interface of a drive system. Input couplers 180 may interface with, and be driven by, corresponding output couplers (not shown) of a telesurgical surgery system, such as the system disclosed in U.S Pub. No. 2014/0183244A1, the entire disclosure of which is incorporated by reference herein. The input couplers 180 are drivingly coupled with one or more input members (not shown) that are disposed within the instrument shaft 106. The input members are drivingly coupled with the end effector 110. Input couplers 180 of the handle assembly can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety. Further details of known input couplers and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties. While described herein with respect to an instrument configured for use with a robotic surgical system, it should be understood that the wrist assemblies described herein may be incorporated into manually actuated instruments, electro-mechanical powered instruments, or instruments actuated in any other way. For example, instrument 100 may include a conventional handle assembly that includes, for example, a stationary handle and a movable handle, which serves as a mechanical actuator for a surgeon to manually operate end effector 110.

Figure 1A:
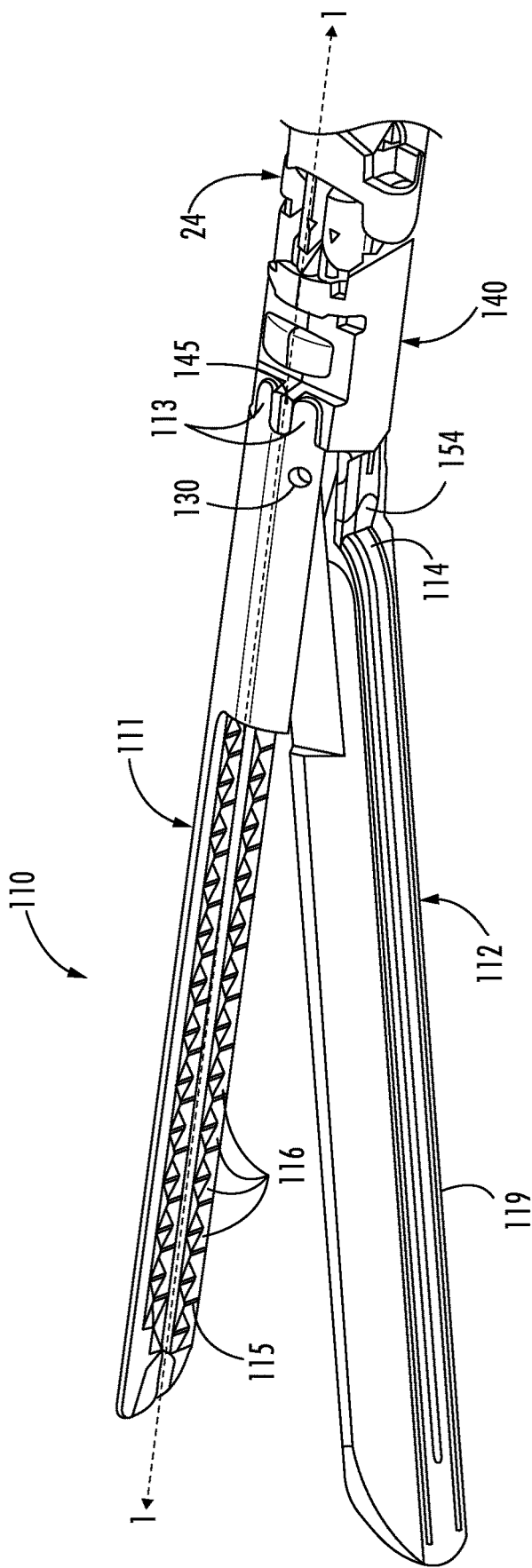
FIG. 1A is a perspective view of the distal end portion of the surgical instrument of FIG. 1 shown having an end effector mounted to an elongated shaft and a backend mechanism configured to actuate the instrument.

FIG. 1A shows the distal end portion of surgical instrument 100, including an end effector 110 defining a longitudinal axis 1-1 and having a first jaw 111, a second jaw 112, a clevis 140 for mounting jaws 111, 112 to the instrument, and an articulation mechanism, such as wrist assembly 24. First jaw 111 includes an anvil 115 having staple-forming pockets 116. In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. In the open position, a fresh stapling cartridge (sometimes referred to as a reload) can be loaded into second jaw 112 and tissue may be positioned between the jaws 111, 112. In the closed position, jaws 111, 112 cooperate to clamp tissue such that the staple cartridge and the anvil 115 are in close cooperative alignment.

Referring now to FIGS. 1B and 1C, a representative staple cartridge 122 may include a plurality of staple assemblies, each comprising one or more staples 124 supported on corresponding staple drivers or pusher 126 provided within respective staple apertures 127 formed in cartridge 122. Of course, it should be recognized that the particular staple cartridge 122 shown in FIGS. 1B and 1C is representative only. Other embodiments of staple cartridge will be known to those of skill in the art. The staple assemblies each include at least one (preferably 2-4) staple pushers 126 removably coupled to at least one (preferably 2-4) staples 124. The staple assemblies are preferably arranged within apertures 127 such that staple pusher 126 is situated near a bottom surface of staple cartridge 122 and staples 124 have their legs facing a top surface of cartridge 122. As discussed above, the entire staple cartridge 122 can be loaded into a jaw of an end effector for use in surgery as described in more detail below. In certain embodiments, staple pusher(s) 126 include one or more supporting elements extending above their top surface for providing support to staples 124 when they are resting thereon. Of course, other suitable geometric designs of staple pusher 126 may be used to receive and hold staple 124 in accordance with the present invention. For example, pusher 126 may have a recess (not shown) for receiving staple 124, as is described in commonly-assigned, provisional patent application Ser. No. 62/855,371, filed May 31, 2019. Alternatively, pusher 126 may have a flatter upper surface (i.e., without a recess or pocket) that allows the backspan of staple 124 to rest thereon, as is described in commonly-assigned, provisional patent application Ser. No. 62/783,460, the complete disclosures of both of these applications are hereby incorporated by reference in their entirety for all purposes.

Cartridge 122 also may include a shuttle 123 having an inclined distal surface 125 that, upon distal movement, sequentially acts on staple pushers 126, camming them upwardly, thereby moving staples 124 into deforming contact with an anvil of a surgical instrument. Shuttle 123 may be part of a drive member 150 (FIGS. 2 and 3) described in more detail below. In certain embodiments, drive member 150 may also include a knife 128 configured to translate distally through a channel 114 in cartridge 122 and to sever clamped, stapled tissue. In embodiments, knife 128 may simply be a sharpened edge on drive member 150 rather than a distinct structure within the cartridge. Cartridge 122 may be removably received within a jaw of a surgical instrument or, in single use embodiments, may be manufactured as part of the jaw.

In certain embodiments, jaws 111, 112 are attached to surgical instrument 100 via clevis 140. Clevis 140 includes upper and lower portions that cooperate when assembled to form a protrusion 145 configured to engage tabs 113 (see FIG. 1A) of jaw 111 to securely mount jaw 111 in a fixed position on instrument 100. Clevis 140 further includes an opening for receiving a pivot pin 130 defining a pivot axis around which jaw 112 pivots as described in more detail below. A more complete description of a suitable clevis 140 for use with the present invention may be found in commonly-assigned, provisional patent application Ser. Nos. 62/783,444, filed Dec. 21, 2018; 62/783,460, filed Dec. 21, 2018; 62/747,912, filed Oct. 19, 2018; and 62/783,429, filed Dec. 21, 2018, the complete disclosures of which are hereby incorporated by reference in their entirety for all purposes. Of course, it will be recognized by those skilled in the art that other coupling mechanisms known by those skilled in the art may be used with the present invention to attach the jaws 111, 112 to the proximal portion of surgical instrument 100.

End effector 110 may be articulated in multiple directions by an articulation mechanism. In certain embodiments, the articulation mechanism may be a wrist assembly 24 as shown, although other articulation mechanisms are contemplated. Preferred embodiments of wrist assembly 24 according to the present disclosure are discussed below in relation to FIGS. 4-11.

As shown in FIG. 2, an illustrative drive member 150 may include a body 151, an upper shoe 152, a lower shoe 154, a central portion 156 and shuttle 123 having inclined distal surfaces 125. Actuation assembly 190 includes a drive cable 171, a coil 120, a sheath 121 surrounding coil 120, and a proximal drive rod (not shown). Drive cable 171 includes an enlarged distal end 173. Upper shoe 152 of drive member 150 includes bore 158 into which drive cables 171 are routed. Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITINOL™, poly para-phenyleneterphtalamide materials such as KEVLAR™ commercially available from DuPont. Those of skill in the art may envision other suitable materials.

The proximal surface of upper shoe 152 is configured to be engaged by a coil 120 of actuation assembly 190 such that coil 120 may apply force to upper shoe 152 to advance drive member 150 distally. A knife 128 may be formed on drive member 150 along the distal edge between upper shoe 152 and central portion 156. Enlarged distal end 173 of drive cable 171 resides within an enlarged distal portion 159 of bore 158 in upper shoe 152 of drive member 150, such that the proximal face 157 of enlarged distal end 173 may apply a retraction force on upper shoe 152 when the drive cable 171 is pulled proximally. The drive rod is operationally connected to an actuator (e.g., input couplers 180), which allows distal translation and proximal retraction of actuation assembly 190. Those skilled in the art will recognize that in a manually actuated instrument, the actuator may be a movable handle, such as movable handle 102b shown in FIG. 1; in a powered instrument the actuator may be a button (not shown) that causes a motor to act on the drive rod; and in a robotic system, the actuator may be a control device such as the control devices described below in connection with FIGS. 12 and 13.

In alternative embodiments, coil 120 of actuation assembly 190 may be coupled with lower shoe 154 instead of upper shoe 152. In these embodiments, coil 120 applies force to lower shoe 153 to advance drive member 150 distally.

Figure 3:
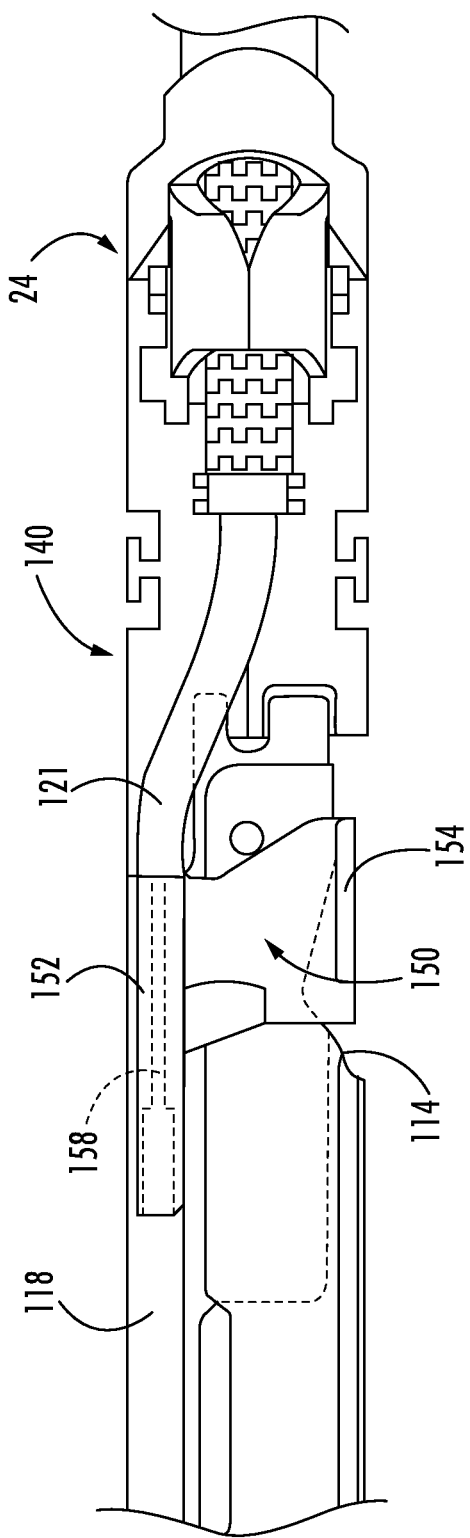
FIG. 3 is a cross-sectional side view of the proximal end portion of an end effector of the illustrative surgical instrument of FIG. 1.

Upper shoe 152 of drive member 150 is substantially aligned with and translates through a channel 118 in first jaw 111, while lower shoe 154 of drive member 150 is substantially aligned with and translates through a channel 114 in jaw 112 and below jaw 112 (see FIG. 3). During actuation of illustrative surgical instrument 100, the drive rod applies force to coil 120, thereby causing coil 120 to apply force to upper shoe 152 of drive member 150, translating it distally initially closing jaws 111,112 and then ejecting staples from a staple cartridge to staple tissue. After stapling is complete, the drive rod may apply a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction. One of ordinary skill in the art will appreciate that drive member 150, drive cable 171, and the drive rod all move in unison and remain in the same relative position to each other.

Upon actuation of the surgical instrument, drive member 150 is advanced distally through end effector 110 to move jaws 111, 112 from the open position to the closed position, after which shuttle 123 and knife 128 are advanced distally through a staple cartridge to staple and cut tissue grasped between jaws 111, 112. Of course, it will be recognized by those skilled in the art that drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through a staple cartridge and upper fixed jaw 111 and lower jaw 112 when the surgical stapling instrument is fired (e.g., actuated).

Figure 4:
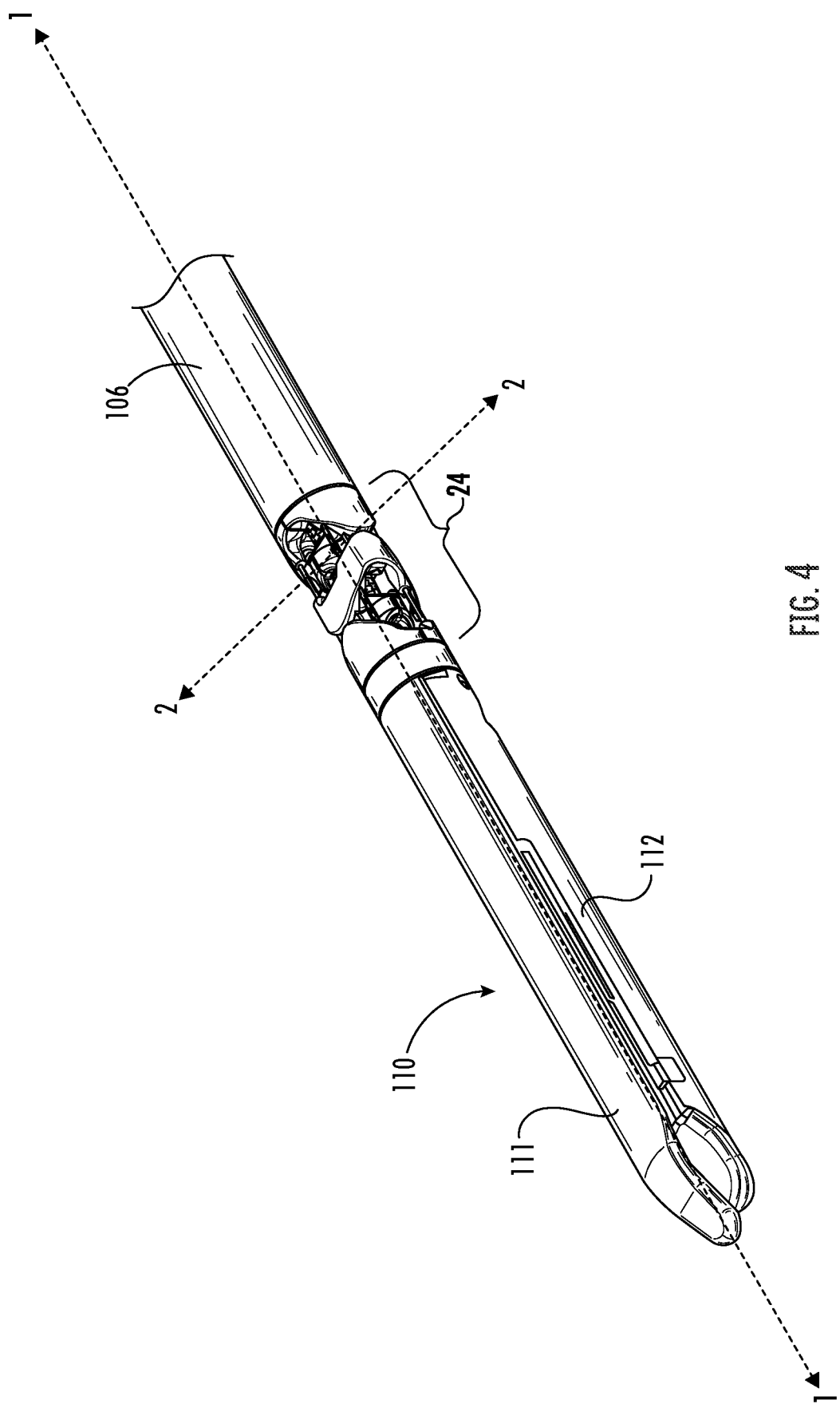
FIG. 4 is a perspective view of the distal end portion of the surgical instrument of FIG. 1 illustrating a wrist assembly according to the present disclosure.
Figure 5:
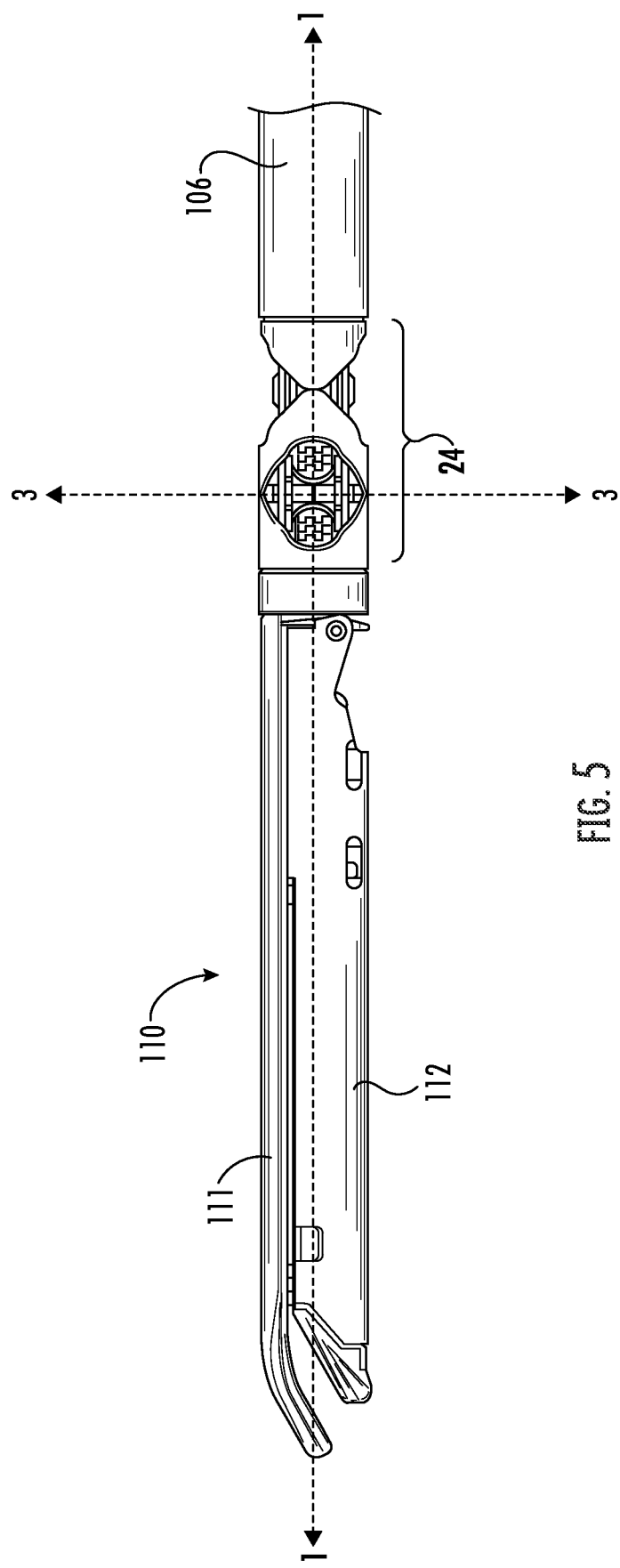
FIG. 5 is a side view of the distal end portion of the surgical instrument of FIG. 4.
Figure 6:
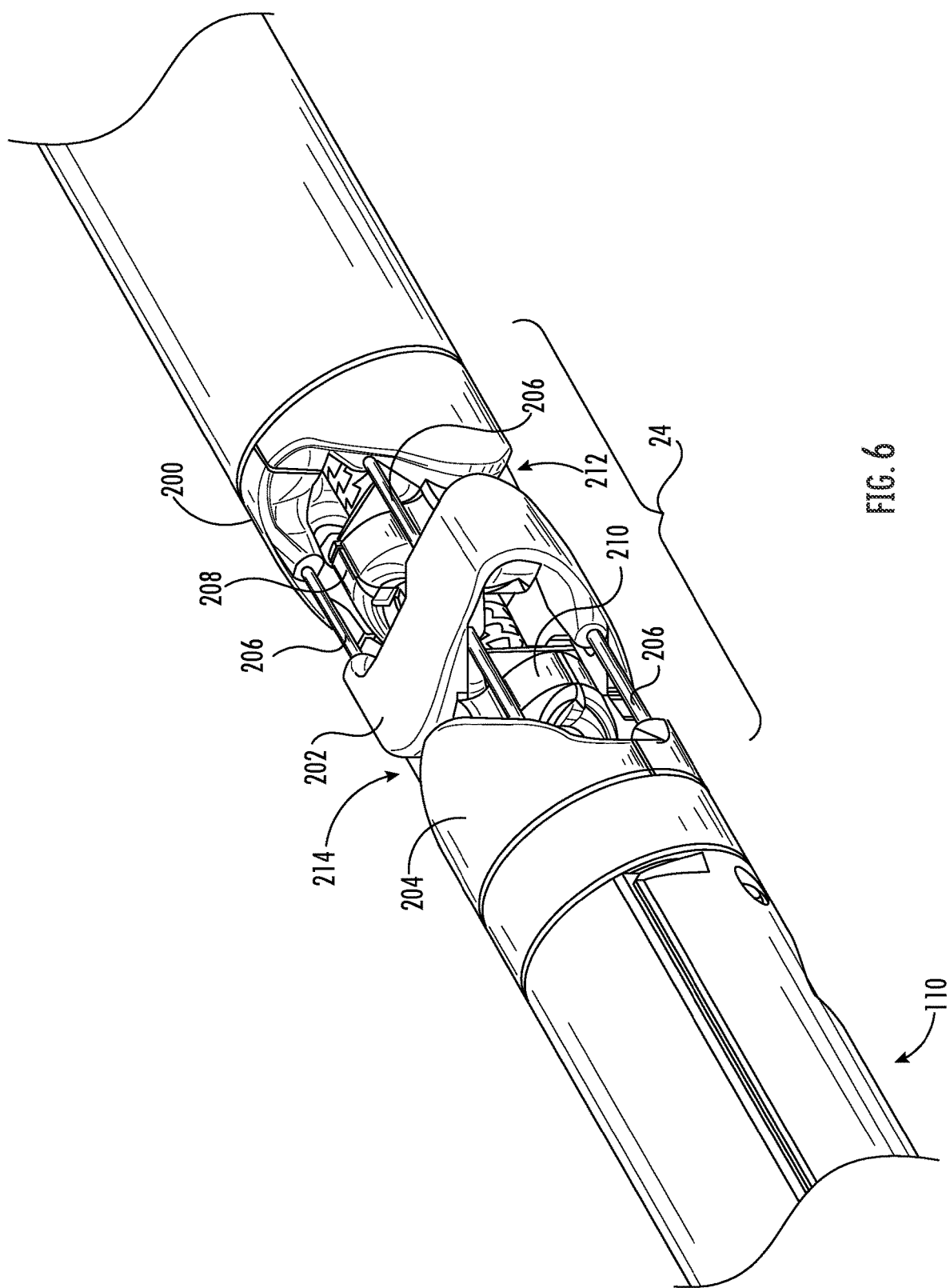
FIG. 6 is a perspective view showing the details of the wrist assembly.

FIGS. 4-6 illustrate a distal portion of surgical instrument 100 that includes a wrist assembly 24 with at least two degrees of freedom and provides for attachment of end effector 110 to elongated instrument shaft 106 for articulation of end effector 110 about at least two orthogonal axes relative to the instrument shaft 106. Wrist assembly 24 is configured to yaw about axis 2-2 (see FIG. 4), which is perpendicular to the longitudinal axis 1-1 of instrument shaft 106. Wrist assembly 24 is also configured to pitch about axis 3-3 (see FIG. 5), which is perpendicular to axis 1-1 and axis 2-2. As shown, the yaw axis 2-2 is proximal (farther from the end effector 110) to the pitch axis 3-3, however this is not a requirement and in some embodiments the yaw axis 2-2 may be distal to the pitch axis 3-3. In certain embodiments, wrist assembly 24 may only be configured to rotate around one or more of the axes 1-1, 2-2 or 3-3.

As shown in FIG. 6, wrist assembly 24 preferably includes a proximal outer link 200, a middle outer link 202, and a distal outer link 204. These three links determine the kinematic pitch and yaw motion of the wrist assembly 24. As shown, the interface between the proximal outer link 200 and the middle outer link 202 defines joint 212 that determines yaw movement of wrist assembly 24. The interface between the outer distal link 204 and the middle outer link 202 defines joint 214 that determines pitch movement of wrist assembly 24. However, in an alternative wrist configuration, this relationship can be reversed such that wrist assembly 24 pitches between proximal outer link 200 and middle outer link 202 and yaws between distal outer link 200 and middle outer link 202 (e.g., by rotating end effector 110 relative to wrist assembly 24 by 90 degrees). In other embodiments, wrist assembly 24 may only include middle outer link 202 and one of proximal or distal outer links 200, 204. In this embodiment, wrist assembly 24 is configured for rotation about a single axis.

Cable portions 206 are drivingly coupled with the wrist assembly 24 and actuated to impart motion to wrist assembly 24. In some embodiments, cable portions 206 can be individually secured to a portion of distal outer link 204. Differential movement of cable portions 206 can be used to actuate wrist assembly 24 to pitch and yaw at various angles. Cable portions 206 can be drivingly coupled to one or more of input couplers 180 shown in FIG. 1. Wrist assembly also includes a proximal inner link 208 and a distal inner link 210 each having a pair of pivot posts 282 formed thereon. Inner links 208, 218 and the function of pivot posts 282 are discussed in further detail below.

Wrist assembly 24 including joints 212, 214 may provide a desired amount of motion, such as +/−90 degrees in a pitch or yaw direction. In embodiments, a single joint 212 can provide up to a 90 degree angular deflection. According to an exemplary embodiment, a wrist may include a plurality of joints 212, 214 to achieve higher ranges of motion (up to roll limit angles), such as, for example, wrists having a range of motion of up to +/−180 degrees in a pitch or yaw direction. Additional details of other joints usable with the embodiments disclosed herein, are disclosed in International Patent Publication No. WO 2015/127250A1, the entire disclosure of which is incorporated by reference herein for all purposes.

Figure 7:
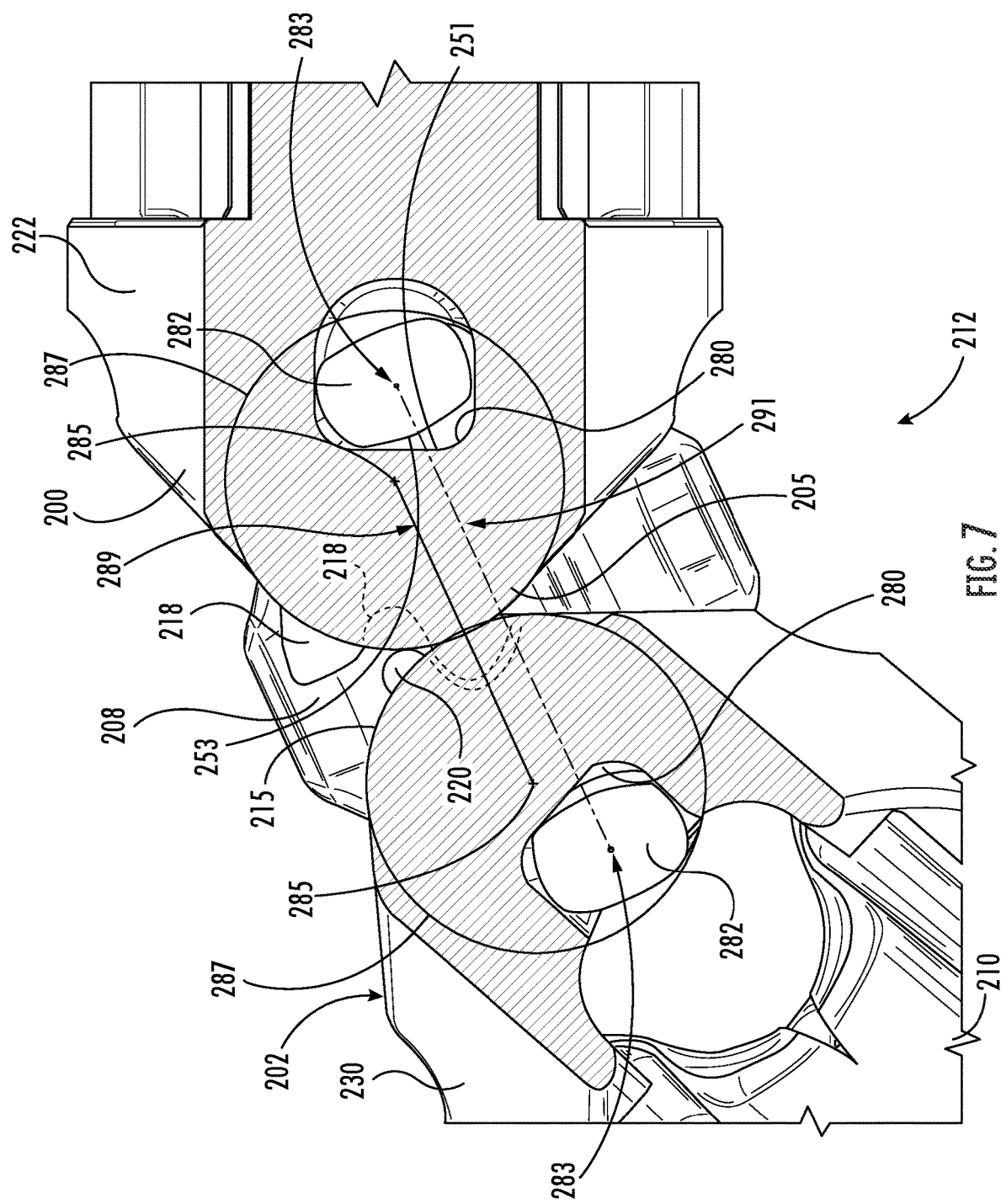
FIG. 7 is a side view with the outer links in cross-section of the proximal joint of the wrist assembly of FIG. 6 in a partially articulated position.

With attention to FIG. 7, proximal joint 212 is shown that is representative of the interfaces between the outer links 200, 202, and inner link 208. Distal joint 214 has a similar construction. Proximal outer link 200 may include one or more gear teeth 218 and a bearing projection 222. Middle outer link 202 includes one or more gear teeth 220 and a bearing projection 230. Gear teeth 218, 220 can provide enhanced timing to assist with accurately positioning outer links 200, 202, including, for example, returning outer links 200, 202 to a neutral position (e.g., zero angle roll alignment), and to enhance smoothness of the motion between outer links 200, 202 such as when outer links 200, 202 are reoriented relative to one another. Bearing projections 222, 230 of outer links 200, 202 may include passages to permit cable portions 206 to pass through. Bearing projections 222, 230 are located at an outboard or lateral location relative to the central apertures 250 of links 200, 202 (see FIG. 8), thereby allowing for routing of other mechanisms (e.g., a drive cable 171) through the central apertures of links 200, 202. Gear teeth 218, 220 engage and disengage during movement to maintain timing (prevent slip) between the rolling contacts. Actuation kinematics between the outer links 200, 202 are determined at least in part by the radius of rolling contacts 205, 215. The bearing projections 222, 230 include curved surfaces 205, 215 that can engage at suitable points throughout all angular motion to help reduce compressive strain on the gear teeth 218, 220.

Proximal inner link 208 may include pivot posts 282 (e.g., configured as protruding journals). The pivot posts 282 are received within and interface with recesses or cutouts 280 (e.g., configured as journal bearings) at medial surfaces of the outer links 200, 202. Together, pivot posts 282 and cutouts 280 define a rocking hinge. A rocking hinge as defined in the present disclosure is a hinge that is not fixed, which means that inner link 208 and outer links 200, 202 do not rotate about a shared axis, as discussed further below.

As shown in FIG. 7, outer links 200, 202 each define an effective rolling radius, which is the distance between the center point 285 of each link 200, 202 to the outer surface 287 of the circle defined by the articulation of each link 200, 202. Outer links 200, 202 further define a centerline 289 that extends linearly between the two center points 285. Pivot posts 282 each have a center 283 and define a separate centerline 291 therebetween. In a conventional fixed hinge joint, the centerline 291 of the pivot posts 282 would always be substantially coincident with the centerline 289 of the joints as links 200, 2002 relative to each other. In the rocking hinge of the present invention, however, centerline 291 of pivot posts 282 moves away from centerline 289 of the joints as links 200, 202 articulate relative to each other. Thus, the centerline 291 of the posts 282 is not fixed to the centerline 289 of the rolling radius of outer links 200, 202, but rather this centerline 291 moves away from the centerline 289 of the rolling radius (in the direction of articulation) as the outer links 200, 202 articulate relative to each other.

In the preferred embodiment, cutouts 280 each have a cross-sectional area that is larger than the cross-sectional area of pivot posts 282. Thus, pivot posts 282 are configured to move within cutouts 280 (i.e., there is sufficient space within cutouts 280 to allow the centers 283 of posts 282 to move or translate relative to outer links 200, 202 during the articulation of outer links 200, 202 relative to each other). Accordingly, inner link 108 moves relative to outer links 200, 202 during articulation of outer links 200, 202 relative to each other. In a fixed hinge, the centers 283 of posts 282 would not move relative to outer links 200, 202 and inner link 208 would rotate about a shared axis with outer links 200, 202.

The rocking hinge of the present disclosure allows for a more compact assembly without sacrificing the internal bend radius of the joint, which offers many advantages. For example, the rolling radii of the links 200, 202 can be reduced without reducing the link or disk length (see FIG. 8), and thereby reducing the internal bend radius that typically results from reducing the size of the rolling radius of a conventional fixed hinge design. Thus, the use of a rocking hinge in a wrist assembly in accordance with the present disclosure allows the designer to reduce the size of the rolling radii without increasing the disk length, thus reducing the overall length of the middle outer link 202 and yielding a more compact wrist assembly. A more compact wrist assembly and, in particular, a smaller rolling radius reduces the potential for tissue pinching to occur, and allows for wrist assembly designs that may not need a cover. In addition, the larger internal bend radius associated with the rocking hinge design of the present disclosure, that is, the amount that the internal components of the wrist must bend, allows for better drive efficiency, less sheath wear, more robust outer tube structures, and improved fitness of the wrist to provide before improved steering forces.

Pivot posts 282 may have a generally rectangular shape as shown, or may be circular, triangular, oval or other suitable shape. Cutouts 280 may include a profile that matches the outer surface of pivot posts 282 or they may be of any desired shape capable of supporting a pivot post 282 as it pivots during articulation. As shown in FIG. 7, posts 282 each have a slightly curved (convex) contact surface 253 configured to contact a substantially flat contact surface 251 on the inner surfaces of cutouts 280 of outer links 200, 202. Each side of proximal inner link 208 may include a pair of commonly aligned pivot posts 282 that interface with the cutouts 280 for a total of four pivot posts 282 per inner link. Each pair of pivot posts 282 is separated to provide an internal passage 244 (see FIG. 11A) for other mechanisms (e.g., a drive cable or mechanism).

Figure 8:
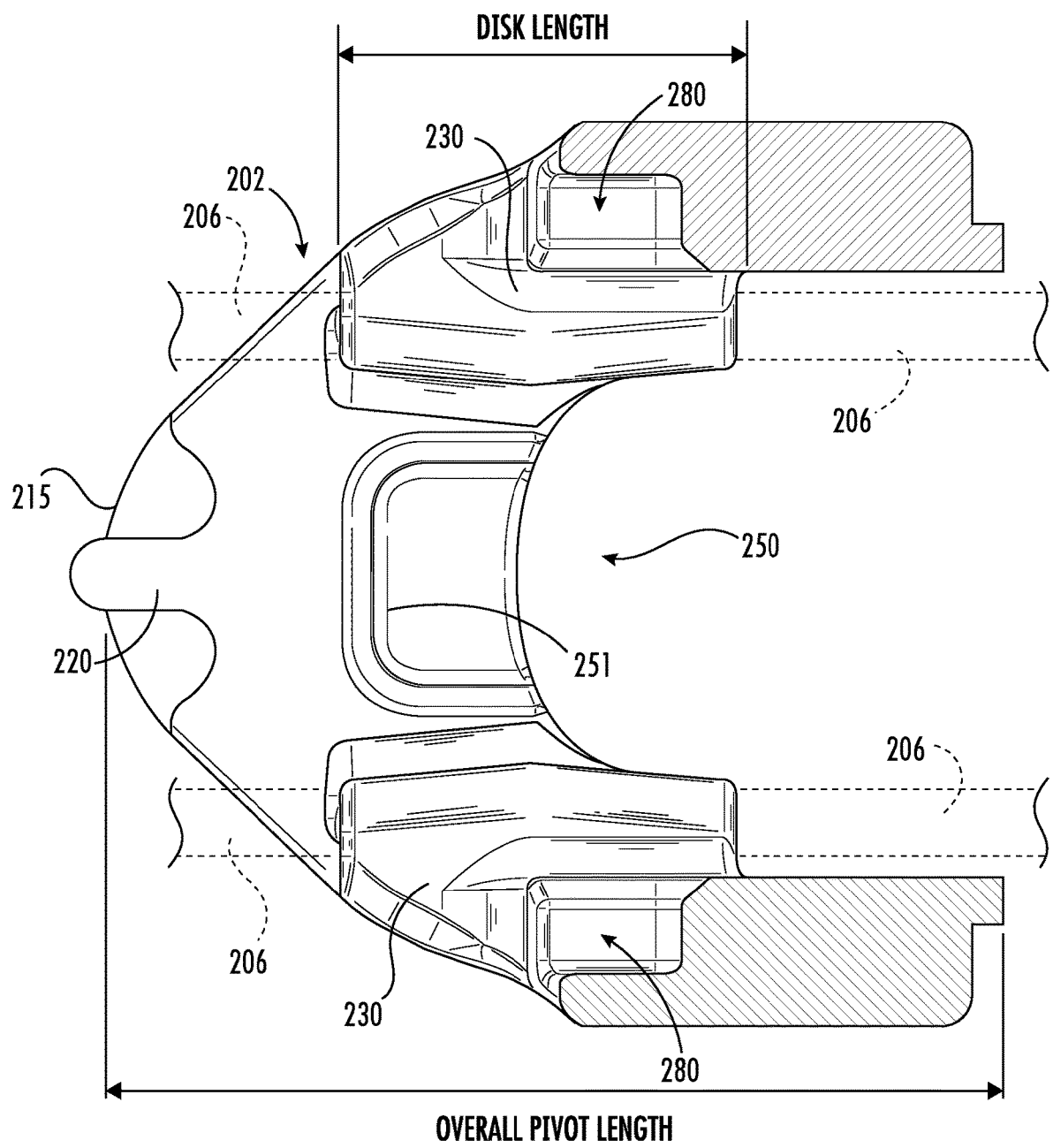
FIG. 8 is a side, cross-sectional view of the middle outer link.

Joint 214 may have a similar construction as joint 212 described above, with inner link 210 joining outer distal link 204 and the middle outer link 202 to form a rocking hinge. It should be understood that only one of hinges 212 or 214 may be a rocking hinge as described herein, with the other of hinges 212 or 214 being a conventional fixed hinge or other suitable design. FIG. 8 illustrates a partial cross-sectional view of outer link 202. As shown, link 202 includes a central aperture 250 for allowing routing of other mechanisms (e.g., a drive cable 171) through wrist assembly 24. Contact surface 251 of link 202 is substantially flat as discussed above. FIG. 8 also illustrates the disk length and overall pivot length of outer link 202. In certain embodiments, the rolling radius of each link can be reduced while maintaining the overall pivot length of the middle outer link. This results in an increased link or disk length, which can significantly improve the mechanical strength of the middle outer link 202 and allow for a more compact design. In other embodiments, the rolling radius of the link can be reduced without increasing the disk length. This results in a reduced pivot length of the middle outer link 202, thereby yielding a more compact wrist assembly.

Figure 9A:
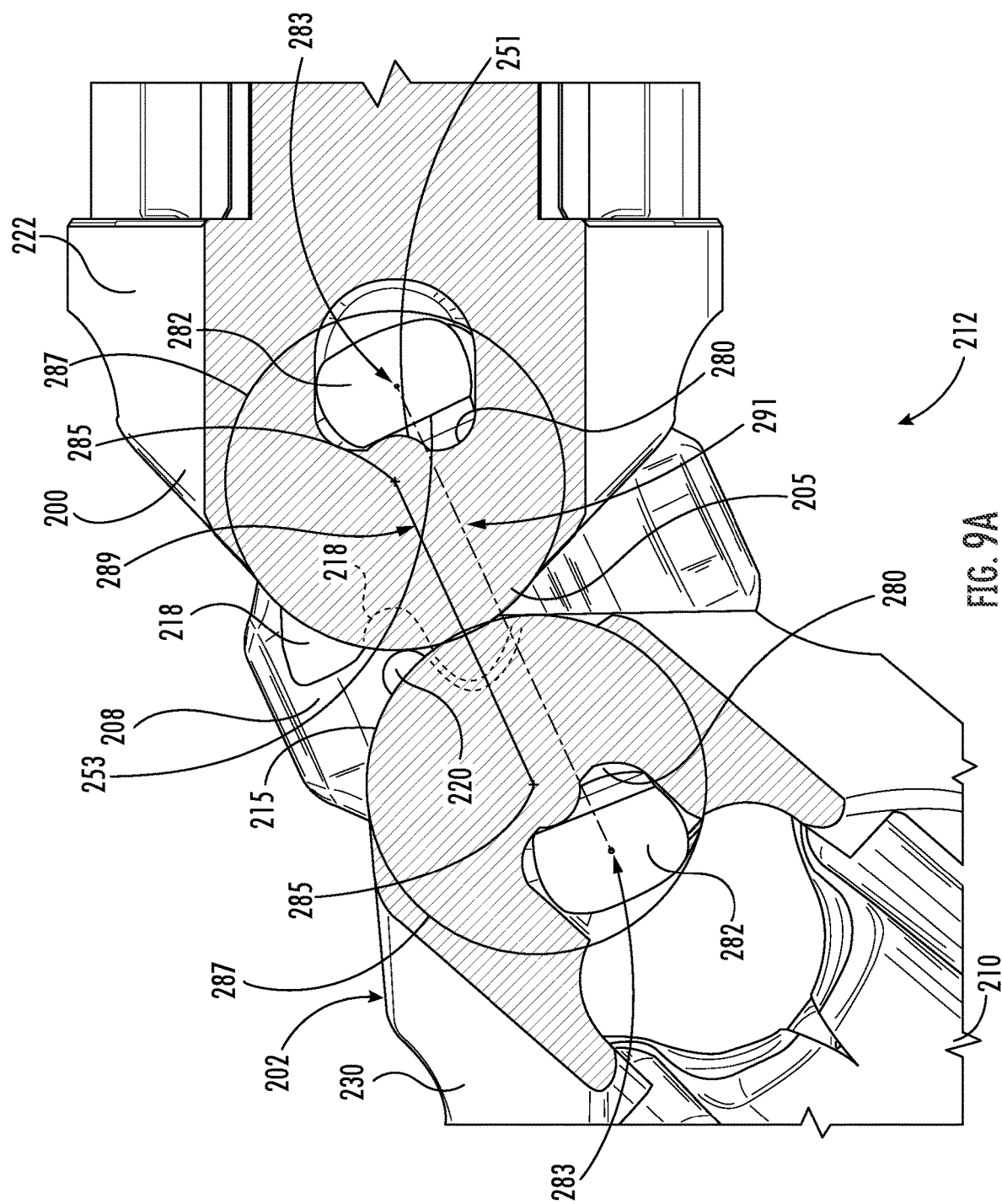
FIGS. 9A and 9B illustrate an alternative embodiment of the proximal joint of the wrist assembly according to the present disclosure.
Figure 9B:
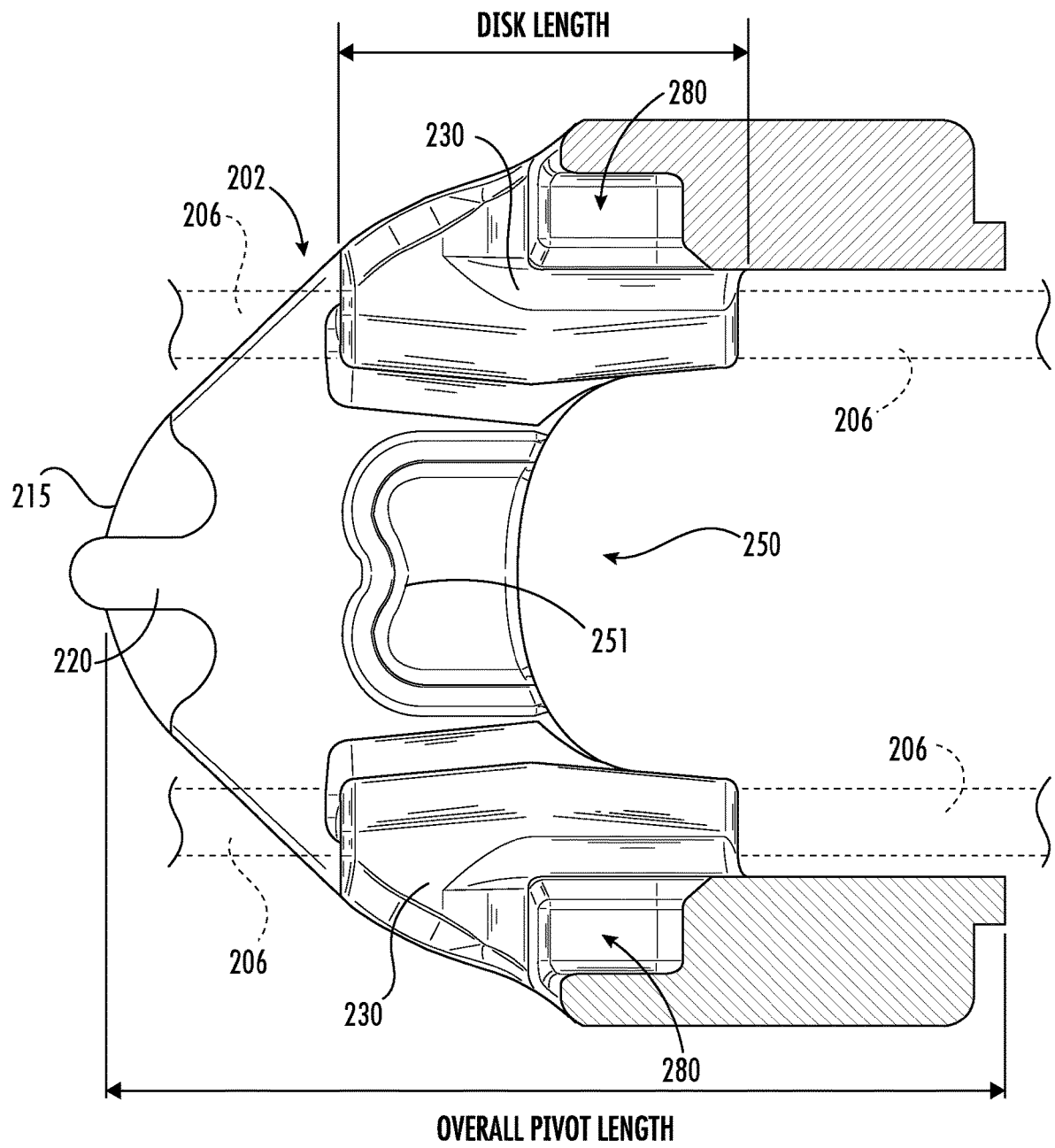

FIGS. 9A and 9B illustrate an alternative embodiment of proximal joint 212. In this embodiment, joint 212 has substantially the same construction as discussed above in relation to FIGS. 7 and 8, expect with reversed contact profiles. As shown, contact surface 253 of posts 282 is substantially flat, whereas contact surface 251 of outer links 200, 202 is curved. Contact surface 251 is preferably a radius that is substantially concentric with the rolling radius of outer links 200, 202. This design provides the benefit that the link maintains contact through a higher range of motion than the design of FIGS. 7 and 8.

Figure 10:
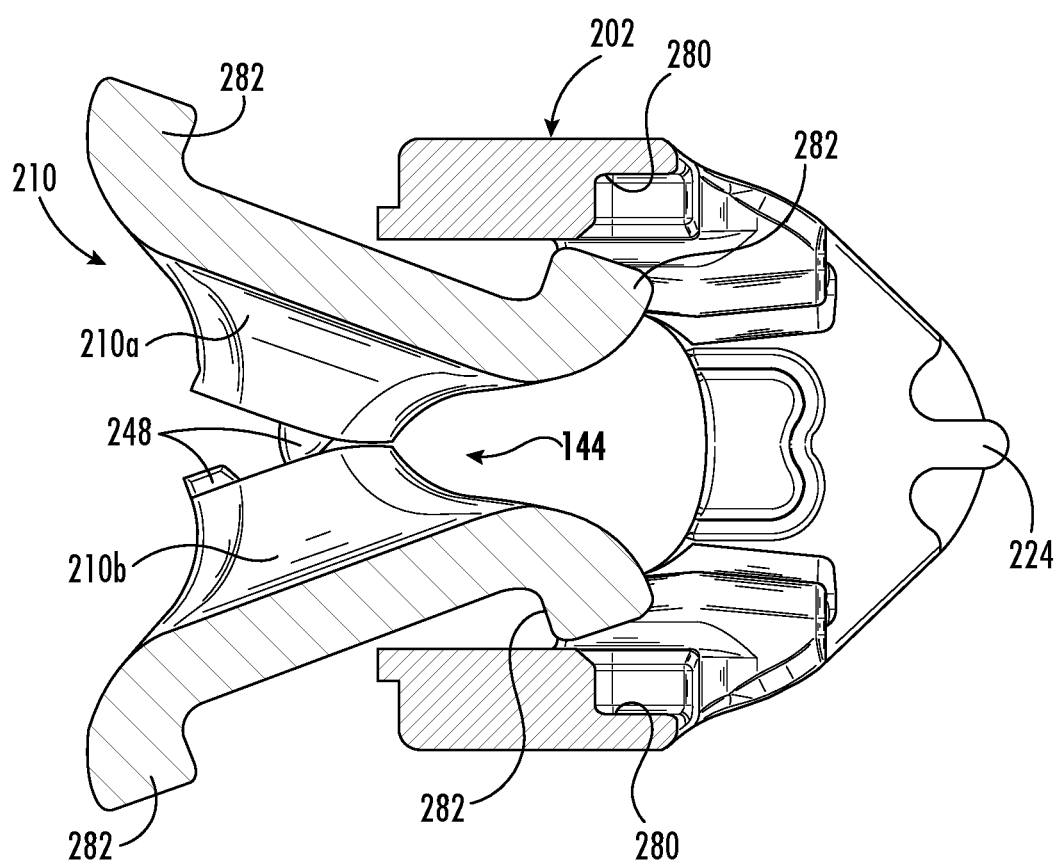
FIG. 10 is a side, cross-sectional view showing assembly of an inner link with an outer link in accordance with embodiments of the present disclosure.
Figure 11A:
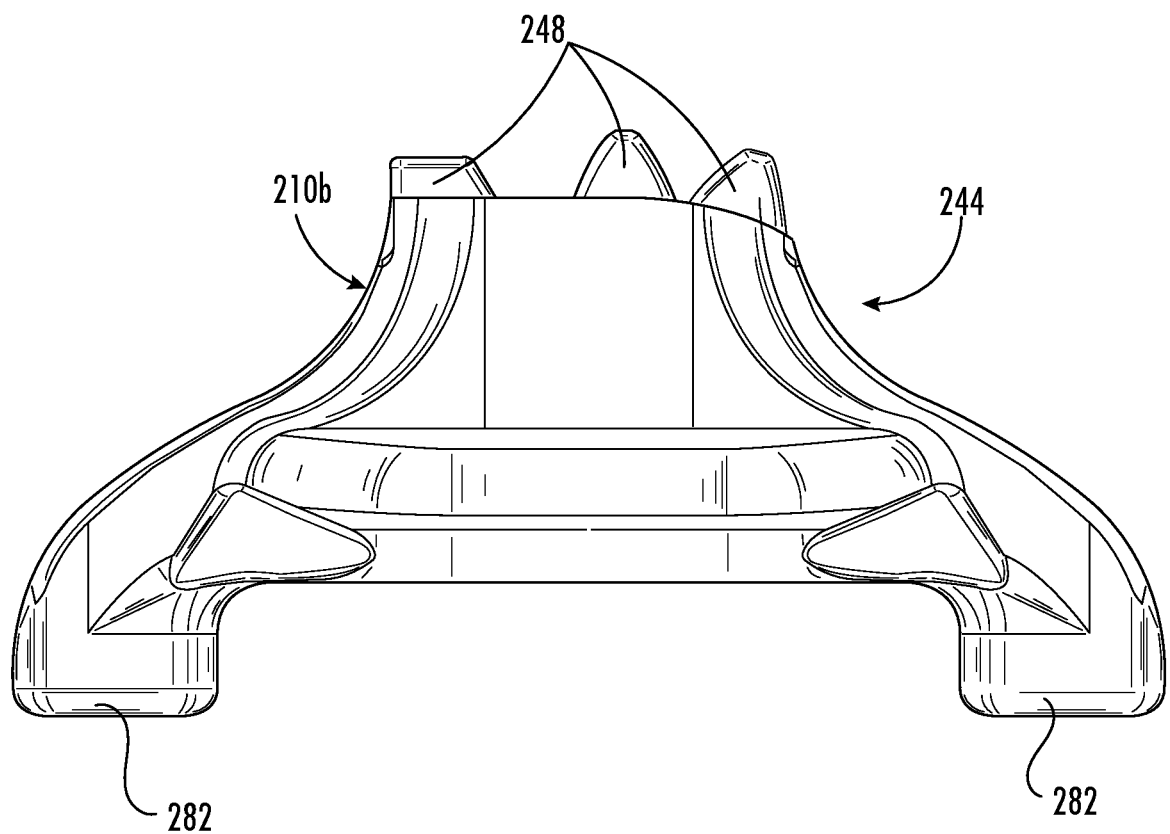
FIGS. 11A and 11B are a side view and a front view, respectively of the two portions that may be assembled to form an inner link in accordance with embodiments of the present disclosure.
Figure 11B:
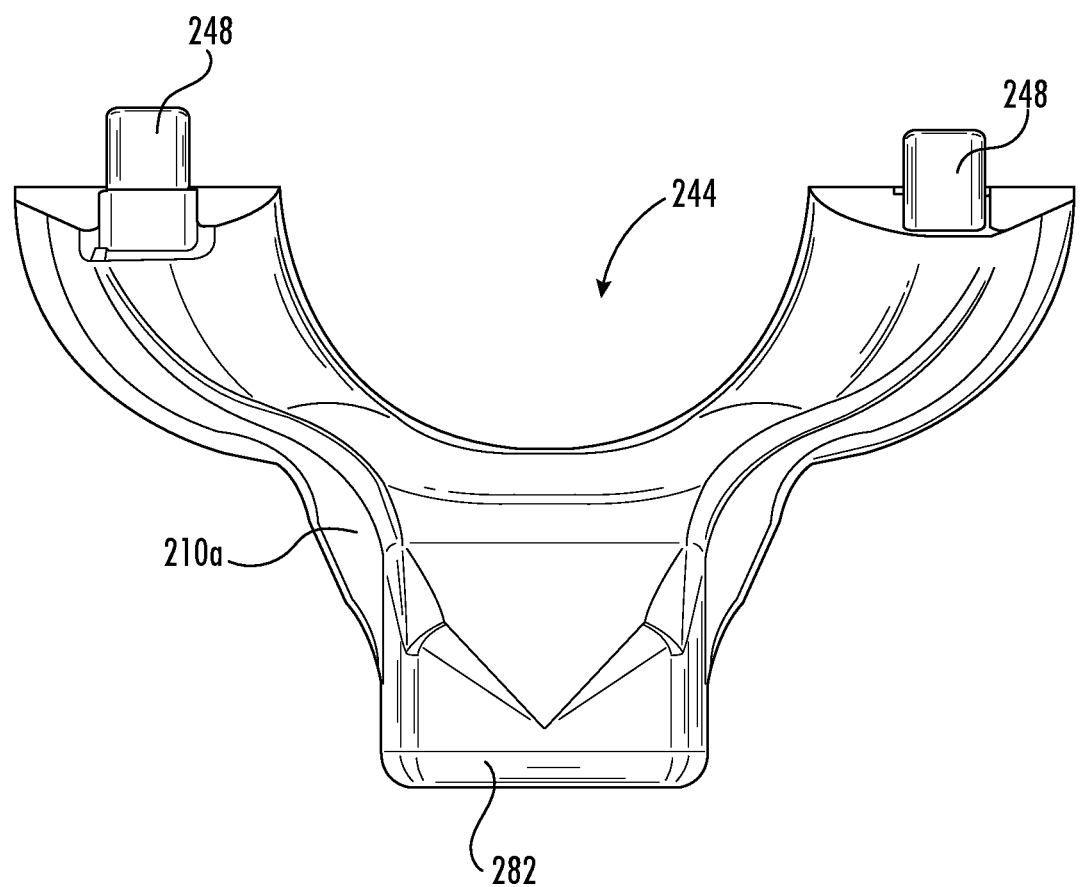

In an exemplary embodiment, each inner link 208, 210 comprises a two-piece construction, as depicted in FIGS. 10, 11A and 11B for inner link 210. These figures also depict a technique for assembling the inner links to the outer links. As seen in FIG. 10, first link portion 210a and second link portion 210b of distal inner link 210 are positioned to place pivot posts 282 into cutouts 280 of middle outer link 202. First link portion 210a and second link portion 210b are inserted at angles such that gear teeth 248 of each portion intermesh to cause alignment of the portions into the formation shown at FIG. 10. Gear teeth 248 are an assembly aid that eliminates the need for pins or other fasteners, and are not used for movement beyond assembly. However, in some embodiments, fasteners can be used in lieu of the gear teeth. After the link portions 210a, 210b are assembled into a complete distal inner link 210, the distal outer link 204 is assembled onto the remaining exposed pivot posts 282 into the formation shown at FIG. 4.

Figure 12:
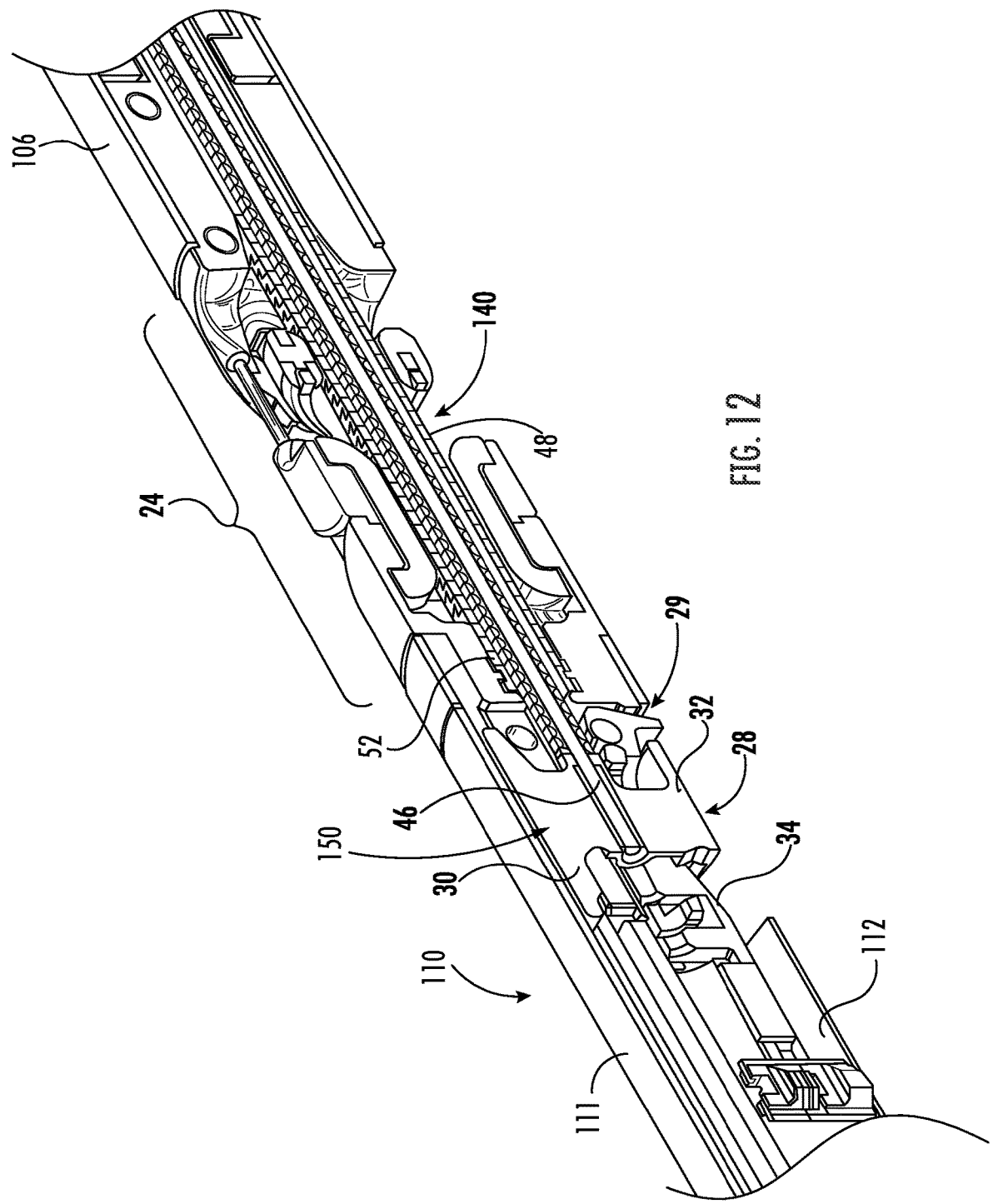
FIG. 12 is a perspective, cross-sectional view showing an exemplary drive mechanism of a surgical instrument in accordance with embodiments of the present disclosure.

FIG. 12 is a partial cut-a-way view of instrument 100, illustrating the interaction between wrist assembly 24 and drive member 150 according to certain embodiments of the present disclosure. In these embodiments, drive member 150 includes a drive rod 46 that slides axially within a sheath 48. An additional sheath 52 may be used to further support the drive rod 46. Additional sheath 52 is fixed to a distal end portion of the wrist assembly 24 and is flexible to bend with movement of the wrist assembly 24, but is constrained from moving axially. Additional sheath 52 and the internal passage provided by the inner links 208, 210 serve to guide and constrain the drive member 150 during axial movement. Additional sheath 52 and the inner passage prevent the drive member from buckling under compressive loading (i.e. distal movement while cutting and stapling). Prior wrist designs, such as disclosed in the aforementioned Int'l. Pub. No. WO 2015/127250A1, rely on tensioned cables to maintain the outer links in position. Inner links 208, 210 serve to prevent separation of the outer links 200, 202, 204 when the driving forces overcome the steering cable tension. Pivot posts 282 of the inner links 208, 210 advantageously maintain the outer links in position when the drive member 150 moves in a distal direction, therefore maintaining the structure of the wrist assembly 24.

As also seen in FIG. 12, a beam member 28 may be driven distally to close movable jaw 112 (shown more clearly in FIG. 1). Beam member 28 can also deploy staples from the cartridge into tissue, and then cut the stapled tissue. Specifically, beam member 28 can also actuate a sled (not shown, but such as disclosed in Pub. No. US 2014/0183244 A1) configured for ejecting staples out of movable jaw 112 during distal movement of beam member 28. Beam member 28 includes an upper beam portion 30 that is configured to slide within fixed jaw 111. Lower beam portion 32 engages a ramp 34 on movable jaw 112 and, upon distal movement of beam member 28, urges jaw 112 towards the closed position relative to jaw 111. Complete closure of the jaw 112 is achieved when the lower beam portion 32 moves distally past the ramp 34. Proximal movement of the lower beam portion 32 off of the ramp 34 removes the closure force applied by the beam member 28. A resilient device or secondary mechanism 29 can then cause closed or partially closed jaw 112 toward the open position. Thus, back and forth movement of lower beam portion 32 along ramp 34 can toggle the end effector 110 between the open and closed positions.

Figure 13:
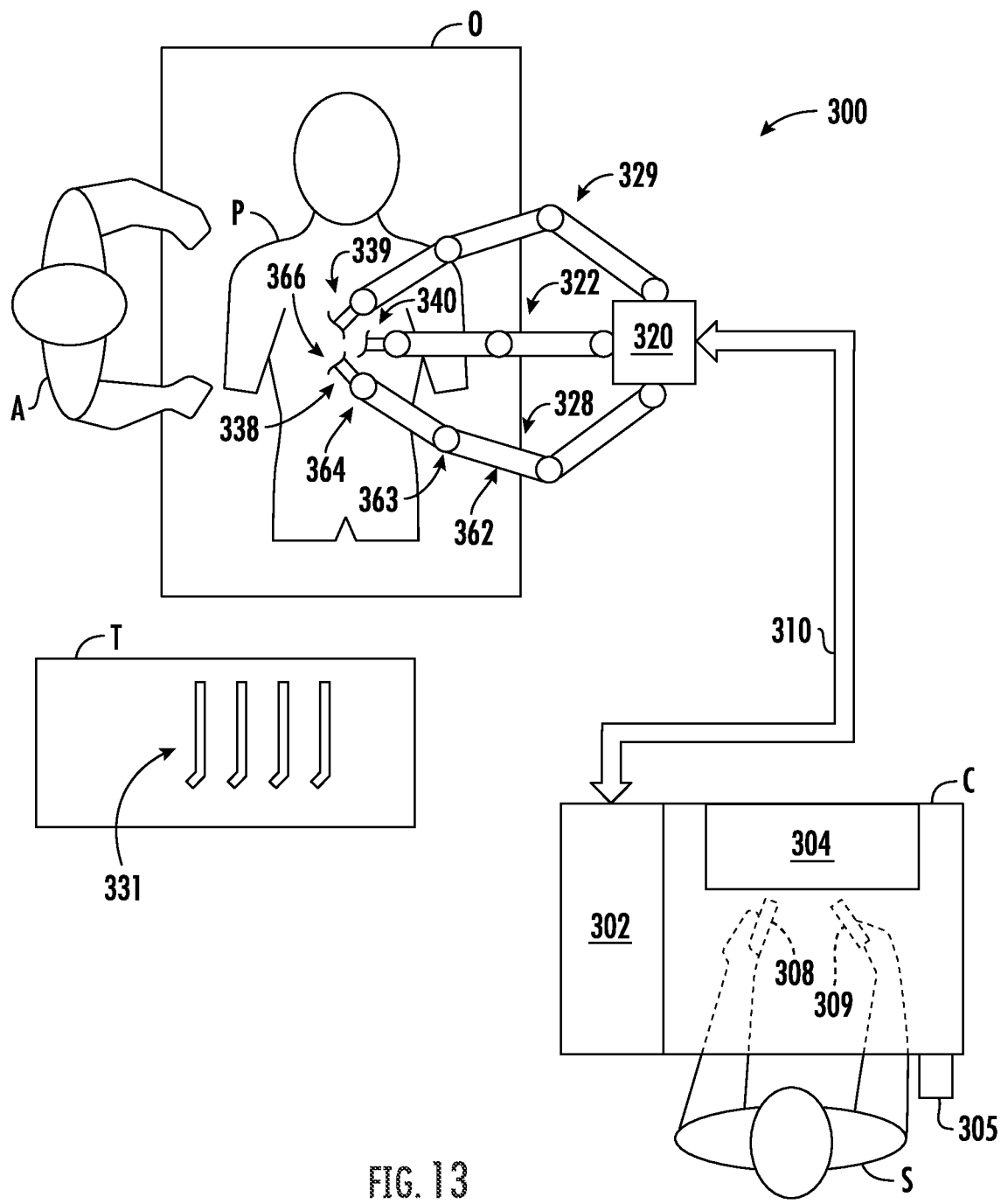
FIG. 13 illustrates a top view of an operating room employing a robotic surgical system utilizing aspects of the present invention.

FIG. 13 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware. For additional details on robotic surgical systems, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are hereby incorporated herein by reference in their entirety for all purposes.

Figure 14:
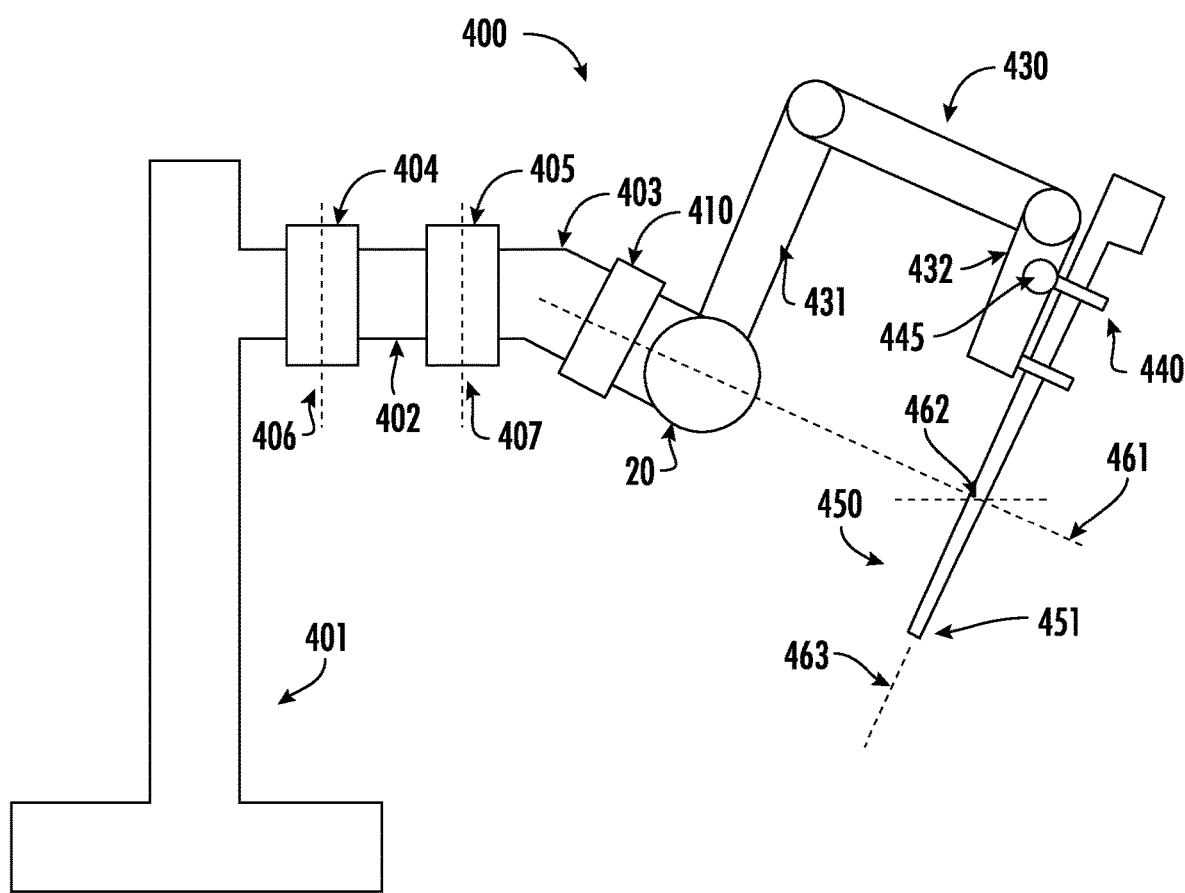
FIG. 14 illustrates a simplified side view of a robotic arm assembly that is usable with various aspects of the present invention.

FIG. 14 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403, which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407. Although only two links and two setup joints are shown in this example, more or less of each may be used as appropriate in this and other robotic arm assemblies in conjunction with the present invention. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator. A more complete description of illustrative robotic surgical systems for use with the present invention can be found in commonly-assigned U.S. Pat. Nos. 9,295,524, 9,339,344, 9,358, 074, and 9,452,019, the complete disclosures of which are hereby incorporated by reference in their entirety for all purposes.

While several embodiments have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical instrument comprising:
an elongated shaft extending along a first axis;
an end effector; and
a wrist assembly moveably connecting the end effector to the elongated shaft, the wrist assembly including:
a first outer link, a second outer link, and a first inner link, the first outer link being connected to the elongated shaft and movably coupled to the second outer link by the first inner link,
wherein the first inner link includes a pair of posts and the first and second outer links each include a recess configured to receive a respective one of the pair of posts, the posts and recesses defining a rocking hinge, wherein the first and second outer links include gear teeth that intermesh.

2. The surgical instrument of claim 1 wherein the rocking hinge is configured such that the first inner link pivots about a separate axis from the first and second outer links.

3. The surgical instrument of claim 2 further comprising a drive mechanism extending through the wrist assembly, wherein the drive mechanism is configured for operation by a robotic surgical system.

4. The surgical instrument of claim 1, wherein the first inner link includes two pairs of posts.

5. The surgical instrument of claim 1, further comprising a third outer link and a second inner link, the second outer link being movably coupled to the third outer link by the second inner link, wherein the third outer link is connected to the end effector.

6. The surgical instrument of claim 5, wherein the second inner link includes a post and the third outer link includes a recess configured to receive the post of the second inner link, the post of the second inner link and the recess of the third outer link defining a rocking hinge.

7. The surgical instrument of claim 5, wherein the second inner link includes two pairs of posts.

8. A surgical instrument comprising:
an elongated shaft extending along a first axis;
an end effector; and
a joint assembly movably coupling the end effector to the elongated shaft, the joint assembly comprising:
a first outer link, a second outer link and an inner link movably coupling the first outer link to the second outer link;
wherein the inner link comprises first and second posts pivotally coupling the inner link to the first and second outer links, respectively;
wherein a center of each of the first and second posts moves relative to the first and second outer links during articulation of the first outer link relative to the second outer link,
wherein the first and second outer links each define a rolling radius with a center and a centerline therebetween; and
wherein each of the first and second posts has a center and defines a centerline therebetween, wherein the centerline between the center of each posts is not coincident with the centerline between the rolling radii of each of the first and second outer links during articulation of the first outer link relative to the second outer link.

9. The surgical instrument of claim 8 wherein the inner link pivots about a separate axis from the first and second outer links.

10. The surgical instrument of claim 8 wherein the first and second outer links have first and second recesses for receiving the first and second posts, respectively, wherein the center of the first and second posts move within the first and second recesses during articulation of the first outer link relative to the second outer link.

11. The surgical instrument of claim 10 wherein the first and second outer recesses each have define an inner cross-sectional area for receiving the first and second posts, wherein the inner cross-sectional area is larger than a cross-sectional area of the posts, allowing movement of the posts within the first and second recesses.

12. The surgical instrument of claim 8 wherein the first and second posts and the first and second recesses define a rocking hinge.

13. The surgical instrument of claim 8 wherein the first inner link includes two pairs of posts, the surgical instrument further comprising a third outer link and a second inner link, the second outer link being movably coupled to the third outer link by the second inner link, wherein the third outer link is connected to the end effector and the first outer link is connected to the shaft.

14. The surgical instrument of claim 13, wherein the first and second outer links rotate the end effector about a second axis substantially perpendicular to the first axis and the second and third outer links rotate the end effector about a third axis substantially perpendicular to the first and second axes.

15. The surgical instrument of claim 13, wherein the second inner link includes a post and the third outer link includes a recess configured to receive the post of the second inner link, the post of the second inner link and the recess of the third outer link defining a rocking hinge.

16. The surgical instrument of claim 8, wherein the end effector comprises a first jaw and a second jaw configured to move relative to each other from an open position to a closed position, the instrument further comprising:
a staple cartridge coupled to one of the first and second jaws and housing a plurality of staples; and a drive member extending through the joint assembly and being configured to translate distally through the end effector, the drive member being configured to engage the staples upon distal translation of the drive member through the staple cartridge and move the staples from an interior of the staple cartridge to an exterior of the staple cartridge.

17. The surgical instrument of claim 16 further comprising:
an actuation mechanism in contact with the drive member and configured to translate the drive member distally through the end effector; and
an actuator operatively coupled to the actuation mechanism, wherein the actuator includes a control device of a robotic surgical system.

18. A surgical instrument comprising:
an elongated shaft extending along a first axis;
an end effector; and
a joint assembly movably coupling the end effector to the elongated shaft, the joint assembly comprising:
a first outer link, a second outer link and an inner link movably coupling the first outer link to the second outer link;
wherein the inner link comprises first and second hinges pivotally coupling the inner link to the first and second outer links, respectively; and
wherein the inner link pivots about a separate axis from the first and second outer links, wherein the first and second outer links include gear teeth that intermesh.

* * * * *